(12) United States Patent
Powell

(10) Patent No.: US 8,343,488 B2
(45) Date of Patent: *Jan. 1, 2013

(54) DIAGNOSIS AND TREATMENT OF HUMAN DORMANCY-RELATED SEQUELLAE

(76) Inventor: Michael Powell, Grass Valley, CA (US)

( * ) Notice: Subject to any disclaimer, the term of this patent is extended or adjusted under 35 U.S.C. 154(b) by 730 days.

This patent is subject to a terminal disclaimer.

(21) Appl. No.: 12/322,488

(22) Filed: Feb. 2, 2009

(65) Prior Publication Data

US 2009/0163448 A1    Jun. 25, 2009

Related U.S. Application Data

(63) Continuation-in-part of application No. 11/978,216, filed on Oct. 18, 2007, which is a continuation of application No. 11/206,564, filed on Aug. 18, 2005, now Pat. No. 7,485,298, which is a continuation-in-part of application No. 10/444,845, filed on May 23, 2003, now Pat. No. 7,288,257.

(60) Provisional application No. 60/382,913, filed on May 23, 2002, provisional application No. 60/383,271, filed on May 24, 2002.

(51) Int. Cl.
    *A61K 39/00*      (2006.01)
    *A61K 39/395*    (2006.01)

(52) U.S. Cl. ............... 424/130.1; 424/198.1; 424/184.1; 424/278.1

(58) Field of Classification Search ............... 424/130.1, 424/198.1, 184.1, 278.1
See application file for complete search history.

(56) References Cited

U.S. PATENT DOCUMENTS 7,485,298 B2 *   2/2009   Powell ..................... 424/130.1

\* cited by examiner

*Primary Examiner* — Ruth Davis
(74) *Attorney, Agent, or Firm* — D. Benjamin Borson; Borson Law Group, PC

(57) ABSTRACT

New methods for diagnosis and treatment of human dormancy syndrome-related sequellae are provided. Human dormancy syndrome (HDS) is characterized by elevated serum ratio of rT3/fT3 compared to a population of normal subjects. HDS includes fibromyalgia, chronic fatigue, cancer, autoimmune disease, obesity and related dormancy conditions. Dormancy and HDS-related sequellae are imposed on humans by infection with lipopolysaccharide (LPS; or endotoxin)-producing organisms, especially those that are intracellular and those that create antigens that stimulate the TLR pathways. In such instances, the elimination or neutralization of the LPS signal along with the infectious source is required to impact the sequellae of HDS. Treatment includes use of novel and non-obvious doses of antibiotics, optionally including agents that decrease the adverse effects of endotoxin.

18 Claims, 6 Drawing Sheets

DIAGNOSIS AND TREATMENT OF HUMAN DORMANCY-RELATED SEQUELLAE

CLAIM OF PRIORITY

This application is a Continuation-In-Part of U.S. Ser. No. 11/978,216, filed Oct. 18, 2007, titled "Diagnosis and Treatment of Human Dormancy Syndrome," Inventor, Michael Powell, now U.S. Pat. No. 7,648,704, issued Jan. 19, 2010, which is a Continuation of U.S. Ser. No. 11/206,564, filed Aug. 18, 2005, now U.S. Pat. No. 7,485,298, issued Feb. 1, 2009, which is a Continuation-in-part of U.S. Ser. No. 10/444,845, filed May 23, 2003, now U.S. Pat. No. 7,288,257, issued Oct. 30, 2007, which claimed priority under 35 U.S.C. §119 to U.S. Provisional Patent Application Ser. No. 60/382,913, filed May 23, 2002, and to U.S. Provisional Patent Application Ser. No. 60/383,271, filed May 24, 2002, titled Diagnosis and Treatment of Human Hibernation Syndrome," Inventor, Michael Powell. Each of the aforementioned applications is incorporated herein fully by reference.

FIELD OF THE INVENTION

This invention relates to methods for diagnosing and treating sequellae related to human dormancy syndrome, including cancer and autoimmune disease. In particular, this invention relates to treating cancer and/or autoimmune diseases using combination therapy using antibiotics.

BACKGROUND

Human Dormancy Syndrome (HDS) is a newly recognized syndrome involving an elevated reverse triiodothyronine ("rT3") to free triiodothyronine ("fT3") ratio and one or more symptoms (see U.S. patent application Ser. No. 10/444,845, incorporated by reference). Diagnosis of HDS was enabled by the recognition that the rT3/fT3 ratio of prior studies was inaccurate, in that subjects considered "normal," in fact, had a disorder as described in the above patent application, the recognition of a lower level of true "normal" subjects, diagnosis of HDS has led to improved treatment.

Cancers are among the most difficult diseases to treat. Cancers are known to be multifactoral, involving genetic predisposition, uncontrollable environmental factors and controllable factors, such as smoking, ingestion of carcinogens etc. Morbidity and mortality exact a large human and economic cost from our society. Current therapies for cancer include chemotherapy using cytotoxic agents, antibodies against cancer cells, and/or radiation therapy, among other treatments.

Early diagnosis of cancer has been one of the more effective determinants of successful anti-cancer therapy. Many methods are used to detect cancer, including histological examination, detection of cancer markers in serum and other bodily fluids, physical examination, patient history, magnetic resonance imaging, positron emission tomography, x-ray, ultrasound and other methods.

However, mechanisms of cancer formation and factors that contribute to cancer growth are not well known. There is general acceptance that certain cancers are associated with mutations in genes (oncogenes) that are present in human cells. Other types of cancers are known to be associated with certain viral infections.

Likewise, autoimmune diseases have a complex etiology, and in many cases, are poorly understood and poorly treated. Thus, predicting the outcome of autoimmune disorders is uncertain, and can lead to ineffective treatments and/or lost time, during which an autoimmune disorder can worsen.

Therefore, there is a great desire to understand the etiology of complex diseases, and development of effective treatments is a major public health concern.

SUMMARY OF THE INVENTION

Thus, one object of this invention is the diagnosis of human dormancy syndrome as well as the tumorgenic, immunologic and infectious consequences that frequently follow dormancy related physiologic changes.

Another object of this invention is to provide effective therapy for conditions related to human dormancy syndrome, and this includes, but is not limited to, the treatment of organisms that exploit the physiologic and immunologic conditions of human dormancy syndrome.

To address these and other objects, embodiments of this invention include the identification that several autoimmune disorders and tumors have striking similarities to HDS. In turn, HDS has similarities to certain fetal conditions. Thus, in certain embodiments, treatment of autoimmune disorders or tumors can be carried out using combination therapy using antibiotics to decrease bacterial infection, which is associated with HDS, autoimmune disorders and certain tumors.

In certain of these embodiments, new regimens for using antibiotics have unexpectedly desirable therapeutic effects, including remission or disappearance of tumors, increased life span, and other beneficial effects. Traditional antibiotic treatment is initiated, and generally, doses of antibiotics are limited to those that provide a desirable killing of the microbes, without causing adverse changes such as the Jarisch-Herxheimer (JH) reaction, which represents release of bacterial products at a high rate and the consequent adverse reactions to those products, including endotoxin. Additionally, when traditional antibiotic therapy has produced the desired bacteriocidal effects and an endotoxin response (JH reaction) has abated, the antibiotic is either continued at that dose, is tapered off or is stopped.

In contrast, in embodiments of this invention, once an endotoxin response has been observed and has abated to a tolerable level, the dose of the antibiotic is increased rather than decreased. This counter-intuitive step permits the antibiotic to enter cells harboring the infective agent and can kill the agent within the cell, and therefore initiate cell death. Certain cancers and autoimmune disorders are associated with intracellular infections. Thus, by use of the counterintuitive step of increasing the antibiotic dose at a time in which the symptoms of systemic infection are abating, one can effectively treat autoimmune disorders or cancers.

What is currently recognized as stress-influenced, noninfectious autoimmune disease is a process related to human dormancy syndrome with secondary exacerbation by lipopolysaccharide ("LPS") (or other superantigen) producing organisms, especially *Chlamydia pneumoniae* (Cpn), *Mycoplasma pneumoniae* (Mpn), *Helicobacter pylori* (Hpi), and/or fungal infections. Diagnosis and treatment of autoimmune disease can benefit from testing and treatment of human dormancy syndrome, cancer, Cpn, Mpn and fungal infections. Measurement of the rT3/fT3 ratio, nitric oxide levels, DHEA-S, free testosterone, estriol, estradiol levels or other variables denoted in Table 1 are helpful for the purposes of diagnosing human dormancy syndrome, and numerous clinical and biochemical tests, including diagnostic markers can be measured (see below) and can indicate presence of cancers associated with infections by Cpn, Mpn, Hpi and fungi. Measurement of sympathetic nervous system hyperactivity using electronic devices designed to measure "stress", such as biofeedback machines, could also be beneficial for diagnostic purposes.

Treatment of Cancer

Embodiments of this invention are based on the surprising finding that in many types of cancer, opportunistic infections with *Chlamydia* (including *Chlamydia pneumoniae* ("Cpn")) are present. Embodiments of this invention are also based upon the surprising finding that many types of cancer are also associated with Cpn are also associated with elevated rT3/fT3 ratio, and thus are related to HDS.

Additional embodiments of this invention are based on the unexpected finding that Chlamydial infections are often associated with HDS. These observations have led to the surprising results that many types of cancer can be effectively treated using anti-Chlamydial agents along with other, conventional antitumor therapies. In other embodiments, co-therapy using anti-Chlamydial agents and treatment for HDS can decrease progression of cancer, can decrease symptoms and in some cases, can eradicate all trace of cancer from subjects suffering from many types of cancers.

Thus, in certain embodiments, cancer therapy can be improved by treatment with antibiotics. In particular, in certain embodiments, flagyl can be used. In prior methods to treat bacterial-associated disorders, the dose of antibiotic has been limited to avoid the undesirable effects of rapid bacterial killing (Jarisch Herxsheimer reaction). However, we unexpectedly found that by selecting patients in whom the adverse reaction has been managed through decreasing endotoxin levels, further increases in doses of antibiotics can be administered that can induce killing of tumor cells. These results have been shown in a series of patients with differing types of tumors.

LPS has been found to stimulate cancer cell growth and impair immune function therefore concomitant treatment with endotoxin (LPS) binding agents, plasmophoresis, dephosphorylating agents or other LPS neutralizing agents are an expected adjunct to the treatment of LPS induced HDS. Other measures include but are not limited to the use of agents that reduce the activity of NF kappa B, kinin, angiotensin (i.e.—ACE inhibitors or ARB's), reduce the activity of COX-2 and PGE2 (i.e.—NSAIDs or omega 3 oils), increase junB activity or lowers HSP70 activity (i.e. ascorbic acid), or increase oxytocin or nitric oxide levels (i.e.—oxytocin, nitroglycerine, Viagra). Treatment with LPS neutralizing agents should be implemented prior to the onset of cancer, bacterial or fungal cell apoptosis inducing therapies.

BRIEF DESCRIPTION OF THE FIGURES

This invention is described with respect to several embodiments thereof. Other features can be found with reference to the Figures, in which.

DETAILED DESCRIPTION

Figure 1:
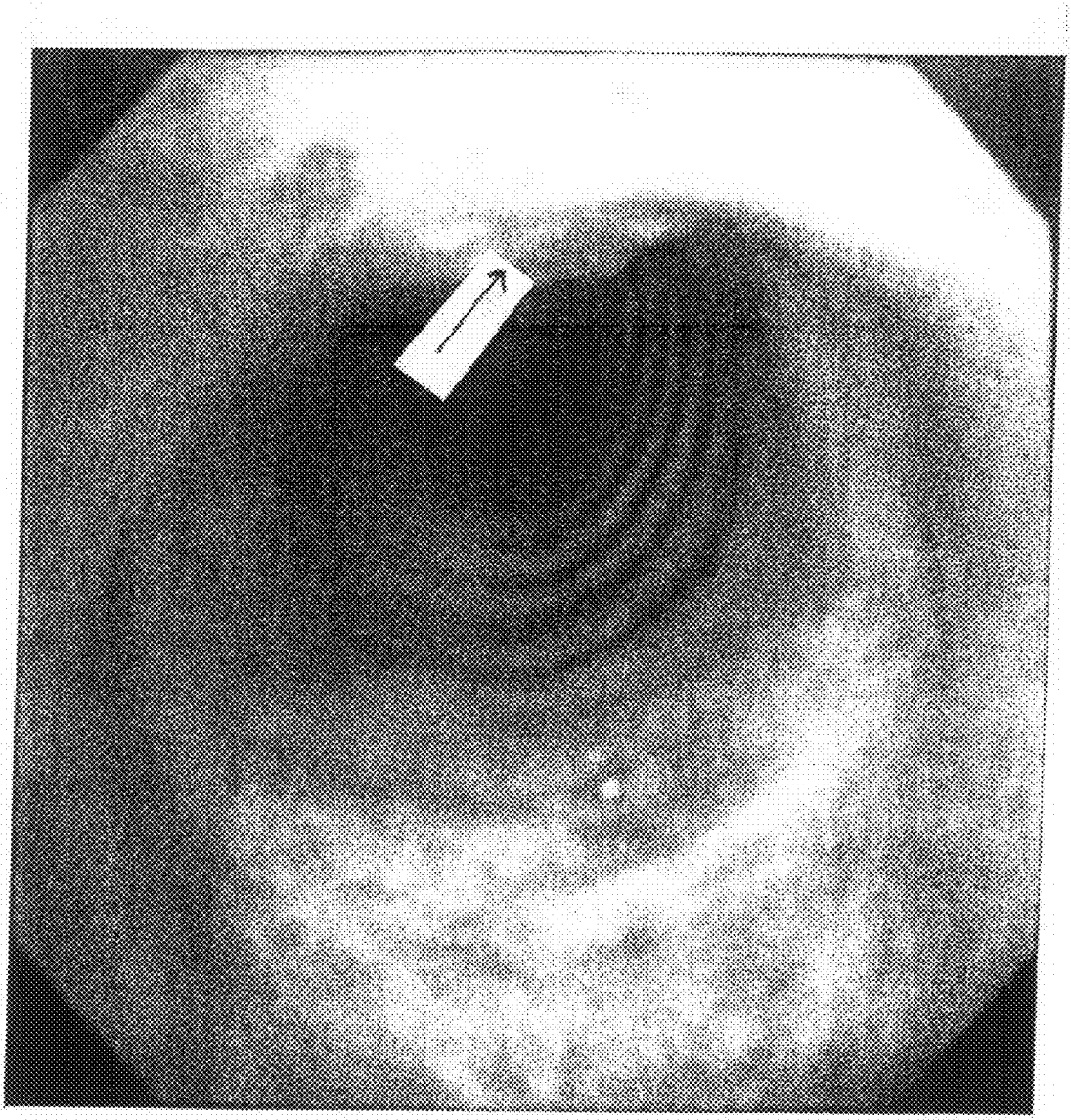
FIG. 1 depicts a photograph of an area of a patient's trachea showing a post-surgical, post-radiation scar before treatment with an antibiotic according to this invention.

Embodiments of this invention are based upon the surprising findings that certain types of cancers are associated clinically and pathophysiologically with infection by *Chlamydia*, for example, *Chlamydia pneumoniae*. Based on this finding, improvement in cancer therapy can be accomplished by treating the Chlamydial infection. In some cases in which conventional anti-cancer therapy has failed, treatment of Chlamydial infection can, without other intervention, result in remission of the cancer.

In other cases, in subjects suffering from cancer and HDS, it can be desirable to treat the HDS along with the cancer.

Hibernating animals express a biochemical phenotype that is remarkably similar to the cellular changes observed in animal tissue during embryonic development, endotoxemia, cancer, autoimmune disease, and other conditions associated with oxidative stress (Table 1).

TABLE 1

Expression of Cellular Proteins in Various Conditions

| | Fetal | Hibernation | Endotoxin | Cancer | Autoimmune | FM |
|---|---|---|---|---|---|---|
| ACE II | Up | Up | Up | Up | Up | ? |
| acetyl CoA carboxylase (ACC) | Up | dec | dec? | Up | ? | ? |
| Adrenal insufficiency | N/A | Up | Up | Up | Up | Up |
| alpha-1-antitrypsin | Up | Up & down | Up, then dec | Up, then dec | Up, then dec | dec |
| Alpha2-macroglobulin | Up | Up | Up | Up | Up | Up |
| alpha-fetoprotein (AFP) | Up | ? | Up | Up | Up | ? |
| angiotensin | Up | dec ? stage? | Up | Up | Up | Blunted response |
| Antithrobin III | dec | ? | dec | dec | dec | ? |

TABLE 1-continued

Expression of Cellular Proteins in Various Conditions

| | Fetal | Hibernation | Endotoxin | Cancer | Autoimmune | FM |
|---|---|---|---|---|---|---|
| Apolipoprotein A1 | dec | Up | binds to ETX | dec | dec | ? |
| Ascorbic Acid | Up beyond maternal | Up | dec | dec | dec | dec? |
| Bcl-2 | Up | ? | Up | Up | Up | ? |
| Bcl-xL | Up | ? | Up | Up | Up | ? |
| beta-endorphin | Up | dec | Acute Up | dec | Up (acute) dec (Chron) | |
| c-fos | Up | Up | Up | Up | Up | Up |
| c-jun | Up | Up | Up | Up | Up | ? |
| C1-esterase inhibitor | Up? | ? | dec | dec | dec | ? |
| calcitonin gene-related peptide (CGRP) | Up? | Up | Up | Up | Up | Up |
| calsequestrin | Up | Up | ? | Up | ? | ? |
| cAMP | Up | Up | Up | Up | Up | ? |
| Carcinoembryonic antigen (CEA) | Up | ? | Up | Up | Up? | ? |
| caspase | dec | ? | dec | dec | dec | ? |
| catalase | Up | Up | Up | Up | Up | Up |
| Cathepsin B (serine protease) | Up | Up | Up | Up | Up | ? |
| caveolin-1 | dec | ? | dec | dec | dec | ? |
| Cholecystokinin (CCK) | Up | varies | Up | Up | ? | ? |
| cIAP-2 (cellular inhibitor of apoptosis-2) | Up | ? | Up | Up | ? | ? |
| connexin 43 | Up | Up | Up | Up | Up | ? |
| corticotropin-releasing factor (CRF) | Up | Up | Up | Up | Up | Up |
| cyclooxygenase-2 (COX-2) | Up | ? | Up | Up | Up | ? |
| cystatin (C inh cathespins) | varies | ? | dec | dec | dec | ? |
| cytochrome-c oxidase | dec | dec | dec | dec | dec | dec |
| D-dimer | Up | ? | Up | Up | Up | ? |
| Dopamine (Vit C dependent) | Up | Up | dec | dec | dec | dec |
| endothelin-1 | Up | Up | Up | Up | Up | Up |
| endotoxin | ? | ? | N/A | Up | ? | ? |
| Enkephalin | Up | Up | Up | Up | Up | Up |
| epithelial growth factor | Up | ? | Up | Up | Up | ? |
| Factor V | dec | dec | dec | Dec +/− | dec | ? |
| FADD (Death Domain) | Up | ? | Up | Up | Up | ? |
| fas ligand | Up | ? | Up | Up | Up | ? |
| fas/APO 1 | Up | ? | Up | Up | Up | ? |
| FLIP (prevents apoptosis) | Up | ? | Up | Up | Up | ? |
| fT3 | dec | dec | dec | dec | dec | dec |
| GABA | Up | Up | Up | Up | ? | ? |
| gap junction activity | Up | Up | Up | Up | Up | ? |
| Gastrin | Up | Up (neurons) | Up | Up | ? | ? |
| Ghrelin | Up | Up | Up | Up | Up | Neither |
| glutathione peroxidase | Up | Up | Up | Up | Up | Up |
| Glyceraldehyde-3-phosphate dehydrogenase | dec | dec | dec | UP!!! | Up!! | dec |
| GSH/GSSG ratio | dec | dec | dec | dec | dec | ? |
| heart type fatty acid protein FABP) | Up | Up | ? | Up | ? | ? |
| heme oxygenase-1 | Up | Up? | Up | Up | Up | ? |

TABLE 1-continued

Expression of Cellular Proteins in Various Conditions

| | Fetal | Hibernation | Endotoxin | Cancer | Autoimmune | FM |
|---|---|---|---|---|---|---|
| Hormone sensitive Lipase (HSL) | Up | Up | Up | Up | ? | ? |
| HPA axis dysregulation | Up | Up | Up | Up | Up | Up |
| HSP70 (Vit C dependent) | Up | Decrease | Up | Up | Up | ? |
| Hypoxia-inducible factor-1 (HIF-1) | Up | ? | Up | Up | Up | ? |
| ICAM-1 | Up | Up | Up | Up | Up | Up |
| IGF-1 (Vitamin C related) | Up | dec 75% | dec | Up | Up | neither? |
| IGFBP inh IGF-1 (inverse of Vit C) | Up | dec | Up | Up | Up | conflict n = 3 |
| IL-6 | Up | ? | Up | Up | Up | Up |
| JNK | Up | Up | Up | Up | Up | ? |
| JunB (Vit C dependent factor) | Up | Up | Up | Dec = bad | dec? | ? |
| kallikrein/kinin | Up | ? | Up | Up | Up | ? |
| lipoxygenase (5-LOX) | up | ? | Up | Up | Up | ? |
| MAPK | Up | Up | Up | Up | Up | ? |
| Mcl-1 | Up | ? | Up | Up | Up | ? |
| Melatonin | Up | dec | dec | dec | UP!!!! | dec |
| moesin/ezrin | Up | Up | Up | Up | Up | ? |
| Na/K-ATPase | Up | decrease | decrease | varies | decrease | ? |
| Neuropeptide Y | Up | Up | Up | Up | Up | Up |
| neurotensin | Up | Up? | Up | Up | ?article pending | ? |
| NF kappa B | Up | Up | Up | Up | Up | ? |
| Nitric Oxide (Vit C dependent) | Up | Dec (varies) | both | dec | Up | ? responds to NTG |
| Nitric Oxide Synthase Not type II) | Up | Dec (varies) | both | Up | Up | ? |
| Norepinephrine | Up | Up then decrease | Up | Up | Up | Up |
| Orexin-A/Hypocretin-1 | ?varies | dec | dec | dec | dec | ? |
| Oxytocin (tissue vs serum) | ?dec | Up in pineal | Up in hypothal. | Up & down | Up in Medulla | dec (Blood) |
| oxytocinase pancreatic triglyceride lipase (PTL) | ?Up | Up | Up (LPL) | Up | Up (antibodies to) | ? |
| PARP | varies | ? | Up | Up | Up | ? |
| Pyruvate Dehydrogenase Kinase (PDK) | ?Up | Up | ? | Up | ? | ? |
| peptide YY | Up | Up? | Up | Up | Up | ? |
| PPAR gamma | Up | Up | dec | Both | Both | ? |
| Prolactin | Up | Up | dec then Up | Up | Up | Up |
| prostacyclin | Up | ? | Up | Up | Up | ? |
| PGE2 (Vit C dependent faCtor, inverse relation) | Up | dec | Up | Up | Up | Up |
| Protein kinase C (Vit C deactivates) | Up | dec | Up, then down | Up | Both | Both |
| Resistin | Up | Up | Up | ? | ? | ? |
| Rho-kinase (ROCK-2) | Up | ? | Up | Up | Up | ? |
| rT3 | Up | Up | Up | Up | Up | Up |
| ryanodine receptor | Up | Up | dec | ? | Up from NO | ? |
| Secretin | Up | dec | dec | Some Cells Up | ? | ? |
| Serine (matrix) Protease | Up | ? | Up | Up | Up | ? |
| Serotonin (Vit C dependent) | Up | Up | Up, then decr | dec? | Up from platelets | dec |
| Substance P | Up | Up | Up | Up | Up | Up |

TABLE 1-continued

Expression of Cellular Proteins in Various Conditions

| | Fetal | Hibernation | Endotoxin | Cancer | Autoimmune | FM |
|---|---|---|---|---|---|---|
| superoxide dismutase | Up | Up | Up | Up | Up | Up |
| survivin | Up | ? | Up | Up | Up | ? |
| Taurine | Up | Up | Up | Up | Up | depleted |
| thrombin-antithrombin complex (TAT) | Up | ? | Up | Up | Up | ? |
| Thyrotropin-releasing factor (TRH) | ?varies | dec | dec | Up on CA cells, serum? | ? | ? |
| thyroxine binding globulin | Up | Up | ? | dec | dec | ? |
| TNF alpha | Up | Up end of hiber | Up | Up | Up | Up & Normal |
| TRAIL | ?Up | ? | Up | dec? | both . . . see decoy | ? |
| tyrosine hydroxylase | Up | Up | Up | Up | Up | ? |
| UCP2 & 3 | ? | Up | Up | Up & normal | ? | ? |
| Vasoactive Intestinal Peptide (VIP) | Up | Up | Up | Up | Up | Up |
| Vasopressin | Up | Up | Up | Up | Up | +/− |
| VEGF | Up | Up | Up | Up | Up | Up if (+) IC |

The presence of the fetal protein moesin in hibernation, cancer and autoimmune disease strongly implicates a similar metabolic process, but additional clues exist with elevated alpha-fetoprotein, and carcinoembryonic antigen levels in fetal tissue, cancer, and autoimmune disease.

It is our contention that all animals enter dormancy in utero, and this process is partially mediated by the placental production of rT3 that exceeds that in the maternal circulation. Animals that are handicapped by aberrant ascorbic acid metabolism cannot enter, maintain or exit the dormant state.

Striking similarities include the presence of moesin in all conditions. Moesin is a fetal protein that is absent in aroused hibernators but elevated during hibernation. Moesin is elevated in cancer, autoimmune disease and most importantly, it is a receptor for lipopolysaccharide (LPS) (also known as endotoxin) interacting with CD14 and Toll-like receptor 4 (TLR4) to trigger the inflammatory cascade. Endotoxin (ETX) is a remarkably conserved bacterial and fungal surface membrane component that is released into the host during infection. Lipid A is the superantigen component of LPS and this moiety has been associated with lethal septic shock, asthma, cancer, autoimmune and heart disease. It is LPS through its interaction with the hibernation mediators moesin, CD14, and TLR4 that initiate HDS and it's sequellae.

The biochemical similarities between the fetal state, hibernation, cancer, autoimmune disease and fibromyalgia depicted in Table 1 are readily evident, and the rare discrepancies between fetal/hibernation metabolism and human disease are directly associated with the loss of an enzyme in humans called gulonolactone oxidase (GLO). GLO is present in the genome for all animals except guinea pigs, fruit bats, and primates including man. It has been hypothesized that a retrovirus may have caused a mutation 35 million years ago impairing GLO synthesis. The result of GLO deficiency is that the final step in ascorbic acid metabolism is absent, endogenous ascorbic acid synthesis is interrupted and ascorbic acid must be obtained from a dietary source. What appear to be anomalous findings in Table 1 are predictable responses in factors that directly or indirectly require ascorbic acid for their synthesis or degradation.

During periods of health the consequences of the GLO deletion may not be as apparent as it is during periods of increased oxidative stress, a condition that increases the demand for ascorbic acid. For example, apolipoprotein A1, a cardioprotective molecule is low in atherosclerosis, endotoxemia, cancer, and autoimmune disease, but it is elevated in hibernating animals and in placental tissue. Not coincidentally, serum ascorbic acid levels are elevated in hibernating animals, especially when arousing from hibernation, and apolipoprotein A1 levels parallel ascorbic acid levels. Similarly, junB is an ascorbic acid dependent factor that is elevated in hibernating animals and animals in utero but is decreased in cancer and autoimmune diseases. Natural hibernation is associated with suppression of PGE2, HSP70, and nitric oxide levels, all ascorbic acid dependent factors, and the opposite is evident in HDS related conditions of endotoxemia, cancer, and autoimmune disease.

The presence of the fetal protein moesin in hibernation, cancer and autoimmune disease strongly implicates a similar metabolic process, but additional clues exist with elevated alpha-fetoprotein, and carcinoembryonic antigen levels in fetal tissue, cancer, and autoimmune disease. It is our contention that all animals enter hibernation or dormancy, in utero. Animals that are handicapped by aberrant ascorbic acid metabolism can not enter, maintain or exit dormancy properly. This is especially true of humans when dormancy is imposed on them by infection with LPS producing organisms. In such instances, the elimination of the LPS signal along with the infectious source is required to impact the sequellae of HDS. Use of the natural signals involved in the arousal from hibernation and dormancy is essential to exist HDS and to treat HDS related conditions. For example, ascorbic acid levels are elevated in hibernation and especially during the arousal phase. Treatment of HDS proceeds more rapidly when ascorbic acid levels are normalized or elevated. Similarly treatment will frequently benefit from the use of agents that increase fT3 as seen in the arousal stage of hibernation and lower rT3 levels. Measurement of the rT3/fT3 ratio easily defines those who will benefit most from normalization of thyroid conversion.

Thus, in most general terms, embodiments of this invention are directed to (1) restoring normal levels of the variables listed in Table 1, along with antibacterial agents in sufficiently high doses to kill intracellular bacteria and other pathological organisms.

Therapy is directed at reversal of fetal metabolism and hibernation would include more than one of the following: lowering ACE activity, increasing alpha-1 antitrypsin levels, lowering alpha 2-macroglobulin levels, lowering alpha-fetoprotein levels, lowering angiotensin II levels, increasing antithrombin III levels, increasing apolipoprotein levels, increasing ascorbic acid levels, lowering Bcl-2 levels, lowering Bcl-XL levels, increasing Bax, Bid and Bad levels, lowering c-fos and c-jun levels, increasing C1-esterace inhibitor levels, lowering CGRP and calsequestrin levels, lowering CEA levels, increasing caspase, lowering catalase and cathepsin B levels, increasing caveolin-1, lowering cIAP-2 levels, decreasing connexin 43, decreasing CRF and COX-2 activity, increasing cystatin, increasing cytochrome-c oxidase, decreasing d-dimer, increasing dopamine levels, lowering endothelin-1, and especially lowering endotoxin levels; lowering enkephalin and epithelial growth factor levels, increasing Factor V levels and decreasing FADD, lowering fas ligand and the fas/APO 1 ratio, lowering FLIP, increasing fT3, lowering gap junction activity, lowering gastrin levels, lowering ghrelin levels and glutathione peroxidase levels, increasing glyceraldehyde-3-phosphate dehydrogenase activity, increasing the GSH/GSSG ratio, decreasing the FABP, lowering heme oxygenase-1 levels, lowering hormone sensitive lipase levels, lowering HSP70, lowering HIF-1 levels, lowering ICAM-1 levels, lowering IGF-1 and increases IGFBP, lowers IL-6 and JNK levels, and increases junB levels, lowers kallikrein and kinin levels, lowers lipoxygenase levels, lowers, MAPK and Mcl-1 levels, increases melatonin levels, and most importantly interruption of the activation of the meosin-ezrin system; increasing the Na/K-ATPase activity, lowing neuropeptide Y and neurotensin levels, lowering NF kappa B levels and increasing nitric oxide levels, increasing orexin-A and hypocretin-1 levels, increasing or lowering oxytocin levels, increasing p53 levels, lowering pancreatic triglyceride lipase levels, increasing PARP levels, lowering PDK levels, lowering peptide YY levels, increasing PPAR gamma levels, lowering prolactin levels, lowering prostcyclin levels, lowering PGE2 levels, lowering protein kinase C and resistin levels, lowering rT3, and increasing ROCK-2 levels, increasing secretin, lowering serine protease levels, increasing serotonin levels, lowering substance P levels, lowering superoxide dismutase and survivin levels, lowering TNF alpha levels, increasing TRAIL activity, lowering tyrosine hydroxylase activity, lowering UCP2 & 3 activity, lowering VIP and vasopressin and VEGF levels.

These mediators of embryonic and dormancy metabolism can be lowered with competitive antagonists, binding proteins, proteasome inhibitors, dephosphorylating enzymes, and other fractionating enzymes or inhibitors such as MG132 which inhibits NF kappa B activation. Agonists that increase the activity or concentration of these biochemicals may include biologically engineered analogs or agents that block inhibitory pathways. Many examples of such agents are well known in the art and need not be described in detail herein.

In general, therapy is designed to first kill systemic, extracellular infections organisms. When this occurs, bacterial endotoxins are released into the body and are associated with several symptoms. Symptoms of sepsis or endotoxemia include hypotension, headache, malaise, tachycardia, fever, chills and then hypothermia, lymphadenopathy, palor, cognitive impairment, seizure, nausea, diarrhea and emesis among others. However, the scope of this invention is not limited to determining the presence of only the above symptoms. Other symptoms and measured variables are known in the art and are included as part of this invention.

Adjunct treatment that facilitates recovery form HDS may also include agent that lower angiotensin, kinin, ACE levels, Bcl-2, Bcl-xL, CGRP, cIAP-2, cathepsin B, connexin 43, COX-2, endothelin-1, epithelial growth factor, FLIP, glutathione peroxidase, HSL, HSP70, HPA-related sympathetic activity, ICAM-1, Interleukin-1, 6, & 12, JNK, 5-LOX, Mcl-1, moesin, NPY, neurotensin, NF kappa B, PDK4, PGE2, substance P, surviving, tyrosine hydroxylase, VIP, vasopressin, VEGF levels and more.

Examples of adjunct agents include ACE inhibitors, captopril, elanapril and the like. Vitamin C (1000 mg 2-4×/day; P.O.), COX-2 inhibitors and/or omega-3 oils to decrease prostaglandin E2 synthesis, Vitamin D, Zn, Mg and Se to decrease NFk-β. Additionally, antibiotics include doxycycline, minocyn, flagyl and the like.

In certain embodiments, the following protocol or a similar one can be used:
1. treat with Amoxicillin or Doxycycline (100 mg/2×/day) or Minocyn (100 mg 2×/day) for 2 weeks; then
2. add Zithromax (250-500 mg 3×/week) or Ketek (100 mg 2×/day) for 2 weeks; then
3. add Flagyl (500 mg 2×/day) for 5 days; then
4. two weeks off Flagyl (maintaining steps 1 & 2 above); then
5. pulse therapy with Flagyl (500 mg 2×/day) for 5 days on, 2 weeks off until symptoms of endotoxemia decrease; then
6. increase the dose of Flagyl to 1000 mg 2×/day or 2000 mg 2×/day until;
7. tumor cell death occurs, as measured via tumor specific markers appear in the appropriate compartment (e.g., blood, urine, etc); and
8. when tumor marker levels decrease to normal values, discontinue treatment.

Management of Endotoxemia

In certain embodiments, it can be desirable to supplement antibiotic therapy with treatments to decrease adverse effects of endotoxin. With the use of such adjunctive treatments, the doses of antibiotics may be increased to higher levels, or more rapidly, because the patient will be protected against at least some of the effects of endotoxin. These types of adjunctive therapies may be directed to one or more of several types of protection against endotoxin. These include:
1) Binding/Digesting Endotoxin to Prevent Recirculation and Accumulation:
  a. Charcoal 10-20 caps at 10 AM, 3 PM and 8 PM, optionally with acidophyssus;
  b. Cholestyramine Powder: 1 pack at 10 AM and one at 3 PM;
  c. High Fiber Diet: Steamed vegetables, brown rice, beans, salad;
  d. Enzymes: Lipram™ or Pangestyme™ having 20,000 USP of lipase per capsule to break down Lipid A in endotoxin. Can be administered 15 minutes before meals or 1 hour after meals. Similase™ is an over-the-counter preparation: 5 capsules before meals.
2) Blocking NF kappa B & Angiotensin with ACE Inhibitors and Nutrition
  a. Zestril™ (lisinopril) 10-40-mg, increase gradually. ACE inhibitors reduce headache, anxiety, depression and appetite. Lowers NF kappa B activity, which controls inflammation;

b. Quercetin™, 500 mg 2×/day. Found in Green Tea, slows growth of pancreatic cancer cells;
   c. Mg, 400 mg 2×/day;
   d. Zn, 30 mg daily;
   e. Se, 200 mg daily.
3) Reduce endotoxin levels: Vitamin C: 500-100 mg 4×/day. Vitamin C drives Cpn into cryptic phase. Vitamin C lowers PGE2 activity and increases apoliproprotein A1. Vitamin C needed for nitric oxide synthase, which can decrease pain. In animals that make Vitamin C, endotoxin stimulates Vit. C. production. Because humans do not make Vitamin C, it must be ingested.
4) Decrease PGE2:
   a. COX-2 Inhibitors. PGE2 is elevated in cancer and coronary artery disease.
   b. Omega-3 oils: 2-3 capsules/day, best in AM if DHA.
   c. Celebrex™ 200 mg/day or aspirin 325 mg/day.
5) Inhibit IL-6-Related Inflammation if Arthritis is Present. For example, use hydroxychloroquine (Plaquenil™); 200 mg ½ to 2×/day.
6) Liver Protection: Thistilyn™, 175 mg 3×/day.

Endotoxin increases PGE2 levels. Inhibiting COX 2 decreases PGE2 formation.

Adjunctive treatments can include agents that neutralize endotoxin (to decrease symptoms of endotoxemia), including plasmapheresis, intravenously administered alkaline phosphatase (e.g., calf-intestine alkaline phosphatase), endotoxin binding protein (EBP; Xoma, Berkeley Calif.), or 5-lipoxygenase inhibitors (e.g., Cingulaire™). Additional adjunctives can be used to decrease or prevent re-absorption of endotoxin from the gastrointestinal tract. Such agents include Questran™, cholestyramine, digestive enzymes (lipase, amylase, protease, e.g., Pangestyme™ or Lipram™; 20,000 U lipase equivalent) delivered 15 minutes before meals P.O. Additional adjunctives include Vitamin C, (1000 mg 2-4×/day P.O. or intravenous), COX-2 inhibitors, Vitamin D, omega-3 oils, Zn, Mg, Se.

Endotoxin neutralizing agents include lipid A hydrolases: ESL04 and ES106 from CloneZyme Library, endotoxin binding protein: NEUPREX (rBPI21, opebacan) from Xoma, CIAP: Calf Intestine Alkaline Phosphatase from Biozyme (Blaenavon, UK), polymyxin B which binds endotoxin, agents which block prostaglandin synthesis=NSAIDs to mitigate early signs of endotoxemia, intravenous infusion of immunoglobulin containing endotoxin binding antibodies (i.e.—Sandimmune or other forms of IVIG) and E5564, a synthetic lipid A analogue from Eisai Medical Research Inc., Teaneck, N.J., USA.

Treatment using the above protocol can continue until a tumor-specific marker indicates tumor cell death. For example, pancreatic cancer can be evaluated using CA 19-9, colon and breast cancers can be evaluated using CEA.

Additionally, endotoxin levels can be measured directly to determine the status of endotoxemia.

Adjunctive measures can also include the use of agents that increase levels of ACC, C1-esterase inhibitor, caspase (especially 8 & 10), caveolin-1, cystatin, cytochrome c oxidase, factor V, FADD, junB, melatonin, nitric oxide, orexin-A, oxytocin, PPAR gamma, TBG, and more. The neutralization LPS and the TLR4 signaling that initiates HDS, the elimination of the infectious agents or environmental sources of LPS, the maintenance of adequate ascorbic acid levels and other metabolic cofactors related to the inflammatory cascade (e.g., hormones, zinc, selenium, manganese, magnesium, vitamins A, B, D and E), has the potential of restoring health to those with HDS related illness by arousing patients from LPS induced dormancy.

Similarly, we have unexpectedly found an association between autoimmune diseases and HDS, and treatment of patients having such disorders can be effectively treated with therapies directed at the HDS itself as well as the immune disorder.

I. Human Dormancy Syndrome

Diagnosis of human dormancy syndrome can be accomplished using clinical history, physical findings, and chemical tests of urine, blood, cerebrospinal fluid (CSF) and/or tissues. Pertinent historical features include symptoms of persistent fatigue, cognitive impairment, weight gain, depression, alopecia, constipation, insomnia, sleep apnea, loss of libido, cold intolerance, exercise intolerance, addiction to stimulants, history of Raynaud's syndrome, dyslipidemia, atherosclerosis, syndrome X, peripheral vascular disease, type II diabetes, Alzheimer's disease (and other dementias), demyelinating disease, (muscle tension headache, migraine), fibrocystic breast disease, breast cancer, prostate cancer, ovarian cancer, other cancers, cholelithiasis, pulmonary artery hypertension, pulmonary fibrosis, COPD, asthma, systemic hypertension, infertility, fibromyalgia, chronic fatigue syndrome, chronic wide spread pain and other chronic pain states, and obesity. (autoimmune conditions such as lupus, scleroderma, rheumatoid arthritis, sarcoidosis, vasculitis, myositis, ankylosing spondylitis, psoriatic arthritis, reactive arthritis, Reiter's syndrome, Becet's and polymyalgia rheumatica, viral, bacterial and fungal infections, septic shock, pneumonia and other serous infections, narcolepsy, hypertension, liver disease, esophageal dysmotility, inflammatory bowel disease, renal disease, Parkinson's disease, coma, impaired stage 4 sleep, irritable bowel syndrome, elevated CRH, elevated sympathetic nervous system activity, dysregulated HPA, low serotonin, altered nitric oxide metabolism and NOS activity, low oxytocin levels, mitochondrial impairment and structural changes with decreased membrane permeability, compulsivity, hypervigilance, dissociation, impaired natural killer cell activity, elevated CSF substance P levels, blunted growth hormone response during provocation testing, orthostatic hypotension, altered cerebral blood flow.

Laboratory findings can include elevated serum rT3 and low serum T3 levels, elevated 5 deiodinase type II (5'-D2) activity, decreased 5'-deiodinase type II (5'-D2) activity, increased mRNA for 5'-D2, decreased mRNA for 5'-D2, increased 3,5,3' triiodothyroacetic acid, low CSF serotonin levels, low CSF melatonin levels and elevated CSF SP levels. Low serum and CSF oxytocin levels and altered citruline levels may indicate altered nitric oxide production.

Thus, according to this invention, a proper normal range can be obtained from non-stressed individuals. By comparing the rT3/fT3 ratio of patients with HDS with a true normal range, an elevated rT3/fT3 ratio can indicate the presence of HDS. Table 2 shows effects of dormancy on physiological systems.

TABLE 2

Effects of Dormancy on Physiological Systems

| Physiological Variable | Dormancy | Fibromyalgia |
| --- | --- | --- |
| rT3 | High | High |
| T3 | Low | Low |
| Serotonin | Low | Low |
| Melatonin | Low | Low |
| Oxytocin | Low | Low |
| Prolactin | High | High |
| Substance P | High | High |
| HPA Axis Activity | High | High |

TABLE 2-continued

Effects of Dormancy on Physiological Systems

| Physiological Variable | Dormancy | Fibromyalgia |
|---|---|---|
| Muscle Weakness | Yes | Yes |
| Exercise Intolerance | Yes | Yes |
| Memory Impairment | Yes | Yes |
| Low Oxygen Consumption | Yes | Yes |
| Female: Male Predominance | Yes | Yes |

II. Treatment of Cancer

Viral genes, called "oncogenes" are often associated with tumorogenesis. However, the immortalizing factor(s) for cancer cells have not been well understood. The known immortalizing (anti-apoptotic) factors include surviving, Bcl-2, and Bcl-xL which impart immunity to cancer cells rendering them invulnerable to chemotherapeutic agents such as cisplatin. Despite an exhaustive literature search we were surprised to find that these anti-apoptotic molecules, which we predicted are central to the survival of hibernating cells during the prolonged oxidative stress of hibernation, have not yet been investigated in the field hibernation research. These anti-apoptotic molecules are activated by LPS through binding with moesin, CD14 and TLR4. By interacting with moesin, CD14, and TRL4, LPS exploits a mechanism used by the host during in embryonic development and during hibernation or dormancy. It is during these periods that immune function is least protective to the host and body temperature decreases. Suppressing the host's body temperature (avoiding fever) during infection would favor bacterial and fungal survival. In that sense, we hypothesize that LPS has evolved as a bacterial and fungal strategy for survival, one that sends an artificial hibernation signal for the host's cells. The host is particularly vulnerable to infection during hibernation. Intracellular pathogens that release LPS and other superantigens that engage TLR4-mediated hibernation and embryonic mechanisms are among the most challenging to defend against.

Our surprising discovery, that the intracellular LPS-producing pathogen Cpn and other organisms are associated with immortalizing many if not most or all cancer cells is novel, and we are the first to demonstrate that anti-*Chlamydia pneumoniae* (anti-Cpn) treatment restores apoptosis to cancer cells and can lead to the spontaneous death of cancer cells. This is especially the case when high doses of metronidazole or other agents are employed to treat the anaerobic "cryptic" form of the organism.

According to one hypothesis, this new understanding is based on one or more of the following findings:

1.) Cpn is ubiquitous and most people are colonized with Cpn or related organisms.
2.) Cpn has an immortalizing effect on the host cells it infects (1).
3.) A low nitric oxide, low ascorbic acid, high oxidative stress (low GSH/GSSG ratio), high rT3/fT3 ratio, environment favors growth of LPS producing organisms, such as Cpn. People with Human Dormancy Syndrome have low nitric oxide levels, partially mediated by an elevated rT3/fT3 ratio as previously described in U.S. Ser. No. 10/444,845, incorporated herein fully by reference.
4.) Patents with fibromyalgia (FM) have low nitric oxide secondary to LPS induced Dormancy. Patients with FM have overgrowth of LPS producing organisms such as Cpn and FM remits with treatment that reverses Dormancy and eliminates LPS and the infectious organisms which produce LPS.
5.) Patients with FM have 50% greater risk of cancer mortality over a 10-year period than those without chronic pain associated with fibromyalgia (FM).
6.) Cpn infection promotes HDS with LPS which influences deiodinase activity, increasing rT3 levels which slows DNA transcription and metabolism in the same manner that placenta rT3 maintains dormancy during gestation.
7.) Elevated plasma and tissue levels of reverse T3 and rT3/fT3 ratio is a feature of many cancers and other Dormancy related conditions.
8.) Cpn infection is recognized as a causitive factor for T-cell lymphoma.

Thus, by eliminating LPS producing organisms such as Cpn from infected cancer cells, apoptosis can be restored and spontaneous apoptosis occurs leading to cancer cell death. Because dormancy favors Cpn growth in many ways and reversing dormancy, for example by raising body temperature to about 100° C. or more and optimizing rT3/fT3 ratio (e.g., by administering T3), favors the elimination of Cpn. Reduced body temperature of no more than 4 degrees is observed in polar bears that are in a state of dormancy referred to as "Walking Hibernation." Body temperature for human beings who have triggered HDS and the related disease states is on average, 97.3 degrees orally, but is often lower, especially during periods of increased stress. Temperatures as low as 95.4° C. have been observed in patients with HDS.

Although fever is normally a feature of disseminated infection, it is not a feature of infection in hibernating animals, nor is it common in subjects having chronic infection with LPS producing atypical organisms such as Cpn. Engaging the host's dormancy response by increasing rT3 levels and inhibiting NOS activity with IL-6, or depleting ascorbic acid levels following prolonged LPS-related oxidative stress, which further impairs immunity can be an adaptive survival strategy for Cpn. Lower body temperature and lower nitric oxide levels can impair WBC function, and these changes can occur when an animal's dormancy or hibernation shift is engaged. Cpn has developed the ability to exploit the host's dormancy defense through the release of LPS, which can increase HSP-60 and HSP-70, especially in ascorbic acid deficient hosts, and can directly impairing mitochondrial function of cells that are involved in mitigating Dormancy. For example, hibernating squirrels have recently been found to cycle out of hibernation every 7 days, presumably to enhance immune function. During the arousal period, a period of high oxidative stress, squirrel ascorbic acid levels increase dramatically. Dormancy that is associated with Cpn-related LPS may not allow for periods of elevated body temperature as seen in uninfected hibernating animals. Arousal from Dormancy may be further inhibited by depletion of ascorbic acid in hosts that lack an endogenous source since increased production of ascorbic acid is a feature of arousal. HDS related conditions are frequently associated with ascorbic acid depletion, as well as abnormal levels of ascorbic acid related metabolites; these abnormalities appear to further impair the host's ability to end Dormancy and are frequently associated pathological processes.

While most DNA mutations lead to apoptosis, cells infected with LPS producing organisms that trigger TLR4 undergo mutation that can be immortalized cancer cells. Elimination of the immortalizing signal from LPS and other TLR4 stimulating superantigens that trigger dormancy and embryonic cellular metabolism, restores apoptosis to these cells, leading to spontaneous apoptosis and death of cancer cells. This is especially true of intracellular LPS producing organisms such as Cpn, especially the cryptic phase of the organism.

Until now, the DNA mutations were assumed to be the sole source of cancer cell immortalization. This assumption would require that all tumor cells have mutations that influence apoptosis, a type of cell death that is associated with caspase synthesis. Since mutations do not always include this system, this explanation is at best, incomplete. Based on our unexpected findings, LPS-related immortalization through Cpn is associated with the ability to immortalize any cell it inhabits, which may apply to a variety of cancer cells. This relationship is supported by the examples described herein of cancer cell apoptosis following comprehensive treatment of Cpn infections in human beings suffering from cancer.

There is little histologic similarity between adenoid cystic carcinoma, colon cancer, and pancreatic cancer. In spite of this apparent heterogeneity, anti-LPS with anti-Cpn treatment lead to apoptosis of each of tumor types. This approach to therapy is effective for a variety of histologically unrelated tumor cells. This supports the concept that LPS-induced HDS, probably through intracellular infection with Cpn, is a potential source for the immortalization of cancer. The ubiquitous nature of Cpn, it's use of LPS, and our unexpectedly broad results supports this hypothesis. Cancer can then be redefined as a condition that may or may not be associated with a DNA mutation in an LPS-triggered, hibernating, embryonically-shifted, proliferating cell that is frequently Cpn infected. Our novel approach to cancer treatment focuses on restoring apoptosis to cells that are influenced by LPS-producing organisms, especially intracellular organisms such as Cpn, by neutralizing LPS and eliminating the HDS perpetuating organism. The presence of the fetal protein moesin in gestation, hibernation, cancer, autoimmune disease, and following LPS exposure supports this relationship. The finding of elevated alpha-fetoprotein, and carcinoembryonic antigen levels in gestation, cancer, and in conjunction with LPS exposure further supports the mechanism of HDS and it's sequellae. High doses of metronidazole may be necessary to eliminate the cryptic phase of Cpn and this treatment can desirably be given in conjunction with other antibiotics, including those that block the extracellular and replication intracellular forms of Cpn along with additional signals that support the arousal from hibernation.

III. Treatment of Autoimmune Diseases

Autoimmune diseases are depicted as a group of diseases involving the immune system in a dysregulated manner to produce an inflammatory process that is ultimately destructive to the body. These diseases may involve all tissues: skin, subcutaneous fat, ligament, muscle, joint, nerve, artery, vein and viscera. The source of these diseases is largely not known. Those who suffer from these diseases are believed to have an underlying genetic predisposition that is triggered by unknown environmental factors. It is believed by some that once the triggering event has occurred, immune dysregulation follows. Some researchers have suggested that it is molecular mimicry that leads to perpetuation of the immunologic reaction in the absence of the original environmental trigger. For example, most patients who develop reactive arthritis after food poisoning with salmonella ingestion have HLA B-27 white blood cell (WBC) surface antigens that predispose them to inappropriate immune response to salmonella. More specifically, a theory proposes that surface proteins from salmonella may induce an antibody and T-cell response that cross reacts with joint tissue in those who develop reactive arthritis.

One theory holds that similarities between the host's cells and the salmonella cells leads to self-attack (autoimmune disease) by the immune system which continues to attack the host's cells after the salmonella cells are eliminated. The theory of molecular mimicry is frequently used to explain conditions where chronic infections cannot be documented as a source of ongoing immune system activity. Autoimmune conditions, such as systemic lupus erythematosus (SLE), have been studied in identical twins who carry identical genetic and immunologic markers for the disease, and yet, the concordance of SLE between identical twins is less than 10%, leading researchers to believe that SLE is caused by a combination of genetic predisposition and environmental triggering from sources that are not currently understood. SLE has been triggered in association with the hormonal changes of pregnancy, emotional and physical trauma, and a number of infections. Once triggered, SLE is considered an autoimmune process that is not driven by an infection, but instead the disease is considered an overactive immune system that is best treated with immunosuppressants. Hashimoto's thyroiditis is another autoimmune condition believed to be caused by antithyroperoxidase antibody production (antibodies that attack thyroid tissue) and lymphocytic infiltration into the thyroid gland, gradually destroying the thyroid cells. Hashimoto's thyroiditis is commonly seen in patients with SLE, although a common mechanism for the two autoimmune diseases does not currently exist. A cure for Hashimoto's thyroiditis does not exist, and the disease is currently allowed to run its natural course to hypothyroidism followed by thyroid hormone supplementation. The current invention proposes a common mechanism for autoimmune conditions as well as novel treatment that is directed at the underlying source of "autoimmune" reactions.

Autoimmune diseases can be exacerbated by emotional and physical stress. Barometric change is sometimes sufficient to trigger a flare-up of rheumatoid arthritis. This phenomena is well-recognized, but the mechanism is not currently understood. This invention provides a mechanism that explains the influences of stress on these diseases and will lead to novel treat approaches for the previously mentioned features of autoimmune disease.

Stress (which includes emotional and physical trauma, infection and inflammation) increases oxidative processes and places a demand on the organism to respond. A biphasic response is frequently observed with acute stress temporarily increasing fT3 levels and reducing rT3 levels for as long as 2 hours in some experimental settings, followed by a decrease in fT3 production, which decreases nitric oxide production; a feature of human dormancy syndrome. Although this response reduces unnecessary loss of body heat and diminishes the need for calories when the stress is cold environmental temperature, this response is maladaptive for most other sources of stress. Nitric oxide is essential for WBC's to combat bacteria and other pathogens. Persons with low nitric oxide levels would be at increased risk of developing infections from commonly encountered organisms that exploit those with low nitric oxide levels.

Processes that activate moesin, CD14, and TLR4 create an environment that favors the growth of organisms that rely on LPS for survival. Chronic exposure to environmental sources of LPS may predispose a host to HDS and increase the risk of bacterial or fungal overgrowth with LPS producing organisms. For example, dried tobacco leaves are high in endotoxin, presumably from mold LPS that accumulates during the drying process. Inhalation of LPS laden smoke promotes localized changes in the lung that favors the growth of LPS producing organisms in those tissues. The LPS related infection would further promote localized HDS-related changes in lung tissue, promoting cancer, an HDS-related sequellae. The detrimental effects of LPS appears to be exacerbated by depletion of ascorbic acid, which is depleted by tobacco smoke and is low in patients with lung cancer. Ascorbic acid has a 30 minute half life, making it especially vulnerable to depletion during prolonged exposure to oxidative stress. LPS producing infections exploit these physiologic opportunities.

*Chlamydia pneumoniae* is such an infection. This commonly encountered organism usually infects through the respiratory route and is able to evade destruction from WBC's in a number of ways, including the use of amphiphysin IIm, a vacuole protein coating that allows this organism to live within, and parasitize macrophages and monocytes, impairing their ability to function properly. Once the organism resides within the WBC's, it is able to disseminate throughout the body to other tissues and cells where is impairs their function. This infection is difficult to diagnose because blood tests for obligate intracellular organisms are commonly false negative. This infection is difficult to treat because curative treatment appears to require that multiple antibiotics be given simultaneously for many months (similar to tuberculosis). Tissue culture for this organism requires special cell cultures that are not often available in commercial settings which further complicates the recognition of *Chlamydia pneumoniae* infection in those with autoimmune disease. Stress lowers nitric oxide and ascorbic acid levels which allows *Chlamydia pneumoniae* to flourish. Infection causes the release of inflammatory mediators that further decreases free T3 and nitric oxide production as described in the human dormancy syndrome, specifically through the effect of inflammatory cytokines on 5' D2 and iNOS activity. Immunologic stimulation triggered directly by the *Chlamydia pneumoniae* antigens can produce vasculitis, arthritis, and other autoimmune features. However, once macrophage function has been impaired by *Chlamydia pneumoniae* infection, the host is made more susceptible to other infectious agents.

In the case of SLE patients, they are susceptible to multiple bacterial infections, including *Neisseria* species and viral infections. What has not been considered is the potential for colonized fungal infections to induce autoimmune disease by providing a constant source of antigenic material for the immune system to contend with. Secondly, immuno-compromised macrophages can allow colonized fungi to disseminate. Fungal culture of the sinus mucosa renders positive cultures for 2-3 different species of fungus in virtually all people. What is different for those with chronic airway disease from those who are asymptomatic is that those with rhinosinusitis have eosinophil activation. Tissue biopsies from symptomatic patients show eosinophic infiltration and elevations in eosinophilic cationic protein levels. These findings are typically present in asthma patients as well as in patients with rhinosinusitis, suggesting the process of fungal mucosal colonization likely extends to the bronchial mucosa. This has led the hypothesis that asthma and rhinosinusitis are one disease and that fungal colonization with eosinophilic activation to fungus is involved in both disease processes.

What has not been explained is why some people become symptomatic with sensitized eosinophils and why others tolerate the colonization. Aspects of this invention are based upon the finding that a drop in nitric oxide production allows *Chlamydia pneumoniae* to disseminate and infect mucosa and macrophages, both of which will impair the host's capacity to control mucosal fungal infection by shifting their metabolic pattern to that of HDS. Other infectious agents, including mycoplasma and more typical bacterial infections, may play a role in asthma and COPD, but the unique nature of *Chlamydia pneumoniae* to live within and compromise macrophages and monocytes makes this infectious agent of central importance. The difficulty in detecting the presence of this organism contributes to the misconception that the diseases it is associated with are autoimmune rather than infectious.

With respect to Hashimoto's thyroiditis, it is possible that the lymphocytic infiltration of the gland is in response to infection of the thyroid gland by fungus or *Chlamydia pneumoniae* and fungus. Fungi possess mitochondria, and mitochondrial function is enhanced by T3. Fungi DNA have T3 receptors, and this makes the thyroid gland a likely target for fungal colonization. Colonization of the thyroid gland by fungus will lead to immunologic activity against the gland. Just as colonization of the intestine with salmonella and exposure of the WBC's to salmonella proteins can induce arthritis, it is likely that the many species of mold that colonize human mucosa can serve as a source of antigens for immune activation. Over 40 species of colonizing mold have been cultured at the Mayo Clinic, and these fungal proteins have thus far not been investigated as a source for autoimmune diseases.

Thus, there is a connection between HDS, *Chlamydia pneumoniae*, and fungal colonization with eosiophilic activation and low-grade systemic fungal infection and processes that are currently considered to be autoimmune. Both *Chlamydia pneumoniae* and airborne fungal spores are ubiquitous, and it is likely that all people are exposed to and colonize these organisms. A competent immune system would likely prevent overgrowth or dissemination of these mucosal colonies. However, stress that is sufficient to trigger human dormancy syndrome will decrease fT3 levels that will lower nitric oxide production that will favor dissemination of *Chlamydia pneumoniae*. Once macrophage function is impaired, additional growth of colonized fungus is likely. The fungal antigens drive immunologic reactions that include vasculitic reactions and type 3 hypersensitivity reactions such as serum sickness as well as the expected type 1-hypersensitivity reactions referred to as atopy. The use of antifungal medication alone is unlikely to be curative when concomitant *Chlamydia pneumoniae* infection and HDS are present and macrophage impairment is ongoing.

The current approach to diagnosis and treatment of autoimmune disease involves a careful history and physical examination followed by confirmatory laboratory tests such anti-CCP antibodies, RF, ANA, ASM, AMA, and anti-dsDNA antibodies, along with C3, C4, urinalysis, CBC and imaging studies where indicated. Once the autoimmune process is identified and the severity of the process is determined, graded immunosuppressive therapy is instituted. The current trend in immunosuppressive treatment has been influenced by the devastating disability that is common when the chronic inflammatory process is not sufficiently suppressed. The current standard of care is to provide aggressive suppression at an earlier stage of the disease than was offered ten years ago.

In view of the relationships that have been described with respect to the biochemistry of dormancy, nitric oxide levels, *Chlamydia pneumoniae* infection and fungal colonization with eosinophil activation, this invention contemplates a new paradigm for the treatment of autoimmune disease. The history and physical exam should include investigation for known signs and symptoms of human dormancy syndrome, *Chlamydia pneumoniae* and fungal infection. Serologic evaluation should seek to document the presence of exposure to both *Chlamydia pneumoniae* and fungal infection, and culture or DNA or other antigen assays should be considered. The rT3/fT3 ratio can assess the degree of shifting toward dormancy and guide the clinician in their assessment of the potential need for treatment of the dormancy component of the illness. Ascertaining systemic and/or local nitric oxide levels will also be of benefit. Serum, plasma or tissue levels of endotoxin (LPS), NF kappa B, angiotensin, kinin, moesin, CD14, activated TLR4, apolipoprotein A1, Bcl-2, Bcl-xL, surviving, CGRP, c-jun, junB, and many other features of embryonic or hibernation related metabolism can help assess the degree of HDS and potential for HDS related sequellae. Measurement of tumor markers and autoimmune markers are also helpful for the purpose of assessing HDS. Physical exam findings of fibromyalgia and tender point tenderness correlates with a reduction in endogenous nitric oxide production. In addition to the standard proven techniques for controlling the life-threatening features of autoimmune disease, measures should be taken to treat dormancy, *Chlamydia pneumoniae* and fungal infections, as these are components of autoimmune disease. Since fungus growth is stimulated by T3, the inclusion of antifungal medication, either topical or systemic, should be considered when reversing dormancy with T3 therapy. Prophylactic antifungal treatment may be helpful when long-term antibiotic therapy is instituted for *Chalmydia pneumoniae* infection.

Following diagnosis, the initial approach to treatment is to decrease LPS and related superantigens as well as block the pathways that are exploited by LPS and related superantigens. It is the signal from the superantigens, rather than the presence of infection that is most harmful to the host. Initial treatment should include LPS neutralizing agents that bind or dephosphorylate LPS rendering it inactive. Oral supplementation with digestive enzymes (including lipase and alkaline phosphatase) can neutralize the component of LPS released from the liver into the bowel with biliary secretions. Plasmapheresis or IVIG for LPS release may also be helpful during aggressive treatment of HDS related bacterial or fungal overgrowth. The normalization of key enzymes and cofactors in LPS related pathways are also an important consideration. For example, NF kappa B activity is elevated in cancer, autoimmune disease, infection, hibernation and gestation. NF kappa B activity is further enhanced by deficiencies in selenium, zinc, magnesium, vitamin D and ascorbic acid, hence these cofactors must be addressed and remain replete during treatment of HDS related conditions.

The use of ACE inhibitors to decrease NF kappa B activity and normalize ACE activity, and lower the elevated angiotensin and kinin levels during treatment facilitates recovery. This is especially important when treating cancer since angiotensin increases the release of Bcl-2 and Bcl-xL, both of which confer immortality on cancer cells. COX-2 activity is elevated in HDS as is the cancer promoting end product of COX-2 metabolism, PGE2. The use of omega 3 oils and ascorbic acid lower COX-2 activity and PGE2 production. The use of NSAID's, especially COX-2 inhibitors is also helpful for HDS related diseases by normalizing another HDS related pathway. 5-LOX activity is elevated in HDS diseases and the use of ascorbic acid and/or 5-LOX blocking agents such as Singulair, reduce leukotriene production and normalize another HDS related pathway. Since the levels of ascorbic acid achievable through oral supplementation are significantly lower than those achievable through IV administration of ascorbic acid, the temporary use of IV ascorbic acid during intensive therapy may be a helpful adjunct in the treatment of HDS related conditions. The intent is to create an environment, with respect to ascorbic acid in this instance, that reflects what is observed in animals arousing from hibernation.

Other measures designed to enhance endogenous nitric oxide production should be considered and these include, but are not limited to, aspirin, oxytocin, arginine, MSM. The treatment of *Chlamydia pneumoniae* infection can require a prolonged period of therapy, including anti-porphyric measures. Calcium channel blockers, which have been shown to enhance the effectiveness of antibiotics against *Chlamydia pneumoniae* by preventing the calcium influx that is necessary for Cpn to remain in the cryptic phase of it's life cycle, may be used in conjunction with antibiotics for patients with *Chlamydia pneumoniae* related autoimmune disorders. Vitamin C has been recently shown to impact Cpn infected macrophages in vitro, driving the organism into cryptic phase. An important therapeutic application of this invention is gene therapy using adeno-associated virus or other suitable vectors to introduce the gene for L-gulonolactone oxidase into the human genome. It is the omission of this enzyme that is responsible for our inability to synthesize ascorbic acid. Restoration of ascorbic acid synthesis would optimize our ability to respond constructively to oxidative stress by allowing for increased synthesis of ascorbic acid and it's metabolites in response to LPS stimulation. The treatment of fungal colonization may include topical antifungal nasal spray and nebulized antifungal solutions or inhaled aerosolized antifungal liquids or powders to reduce the burden of fungus growth at these sites, while systemic antifungal medication is necessary for the treatment of disseminated fungal infections, including Hashimoto's (fungal) thyroiditis. Thyroid needle biopsy may be necessary for diagnostic purposes to obtain tissue confirmation using either bacterial/fungal DNA assays or culture of both for *Chlamydia pneumoniae* and/or fungus. These diagnostic techniques and treatments are not currently applied to autoimmune disease processes, and this approach represents an advance toward palliative and/or curative treatment for autoimmune disease. More effective treatments for *Chlamydia pneumoniae* and fungal infections, as well as the development of new medications to prevent dormancy-related physiologic changes, as described in U.S. patent application Ser. No. 10/444,845, incorporated fully by reference, are also beneficial to patients with autoimmune disease. Table 3 shows relationships between fibromyalgia, traumatic stress disorder and dormancy.

TABLE 3

FM, Post Traumatic Stress Disorder and Dormancy

| | FM | PTSD | DORMANCY |
|---|---|---|---|
| Slow Wave Sleep Impaired | Yes (8, 11) | Yes (12-14) | Yes (196, 197) |
| Irritable Bowel (IBS) | Yes (15, 16, low VIP 199, 200) | Yes (15, 17, 18) | Yes, low VIP (198) |
| HPA Dysregulation | Yes (19-22) | Yes (23-26) | Yes (200, 201) |
| High CRH | Yes (27, 28) | Yes (29-31) | Yes (202, 203) |
| Sympathetic Hyperactivity | Yes (32-34) | Yes (32, 35-38) | Yes (204, 205) |
| CSF Substance P | Increased (39-41) | Increased (42-44) | Yes (206, 207) |
| Pain Perception | Increased (45-47) | Increased (48-50) | ? |
| Serotonin | Low (51-53) | Low (54-56) | Yes (208, 209 |
| Prolactin | Increased | Increased | Increased |

TABLE 3-continued

FM, Post Traumatic Stress Disorder and Dormancy

|  | FM | PTSD | DORMANCY |
| --- | --- | --- | --- |
| Growth Hormone Response | Blunted (61-63) | Blunted (64) | Yes (210, 211) |
| Oxytocin | Low (65, 66) | Low (67-70) | Yes (212, 213) |
| Nitric Oxide Metab Abnormal | Yes (39, 52, 71) | Yes (71, 72) | Yes (214, 215) |
| Cerebral Blood Flow | Centralized (73-75) | Centralized (76-79) | Yes (216, 217) |
| Cognitive Function | Impaired (80-82) | Impaired (83-86) | Yes (131.1, 218) |
| Orthostatic Hypotension | Yes (87-89) | Yes (88) | ? |
| Fatigue | Yes (90-92) | Yes (93-95 | Yes (219, 220) |
| Exercise Intolerance | Yes (96-98) | Yes (99, 100) | Yes (221, 222) |
| Mitochondrial Impairment | Yes (97, 102, 103 | Yes (101) | Yes (223, 224) |
| Hypervigilance | Yes (104-106) | Yes (26, 107-109) | Yes |
| Compulsivity | Yes (15, 110) | Yes (15, 111, 112) | ? |
| Detachment/Dissociation | Yes (82, 113) | Yes (107, 111, 114) | ? |
| Depression/Anxiety | Increased (116-118) | Increased (117, 119) | ? |
| Significant Emotional Trauma | Yes (121-125) | Yes (95, 126, 127) | N/A |
| Impaired NK Cell Activity | Yes (128-130) | Yes (131) | Yes |

References are included in parentheses.

Embodiments of this invention include measurement of endotoxin and related bacterial and fungal surface superantigens, NF kappa B activity, ACE activity, CD14 levels, moesin levels, Bcl-2 or Bcl-xL levels, *Chlamydia pneumoniae* and/or fungus antibodies, or direct culture of these organisms or testing of antigens, immune complexes or DNA from these organisms. Thus, in certain aspects of this invention, the treatment of human dormancy syndrome, *Chlamydia pneumoniae* and/or fungus can be beneficial for treating underlying causes of autoimmune diseases.

Aspects of this invention are based on the new observation that several medical conditions, including cancer and autoimmune disorders heretofore unassociated with each other have a common etiology: HDS, with secondary infection by *Chlamydia pneumoniae* and/or fungus.

EXAMPLES

The examples that follow are intended to illustrate aspects of the invention and are not intended to limit the scope of the invention.

Example 1

Case Report: Antibiotics Eliminate Adenoid Cystic Carcinoma

A 41-year old male non-smoker developed gradually worsening dyspnea most noticeable while exercising in July 2000. Pulmonary Function Testing (PFT) revealed an abnormal flow volume loop consistent with airway obstruction. Laryngoscopic examination confirmed the presence of a sizable mass 1 cm below the vocal cords and CT scan showed greater than 80% obstruction of the airway Referral to an ENT physician was obtained and excisional biopsy was performed. Pathological examination confirmed the presence of Adenoid Cystic Carcinoma (ACC) with cribiform diploid cells (will use precise wording when report is available). The Tumor Board reviewed the case and laryngectomy was considered but not recommended at that time because the tumor margins extended beyond the trachea into the paratracheal fat making surgical cure unlikely. This malignant tumor typically travels along nerve sheaths, such as the recurrent laryngeal nerve, to distant sites. The lungs therefore are frequent sites for metastasis. Laryngectomy has not been shown to extend survival in most cases. The mean survival for diploid ACC is 117 months.

It is generally known that ACC is not usually sensitive to chemotherapy or standard proton beam radiation. Higher energy radiation doses, such as neutron beam radiation, have shown some promise and referral to the Cancer Center for radiation treatment was arranged. Under the care of a physician, 16 sessions of neutron beam radiation were provided, followed by two sessions of endotracheal brachytherapy with proton radiation. The patient tolerated the radiation relatively well and returned to work. He was warned that chronic bronchitis might follow airway radiation from the loss of salivary cells and ciliary cells in the bronchus. The patient was screened for recurrence twice yearly with neck MRI and lung CT for 3 years and there was no evidence of recurrence. Post radiation year 4 brought recurrent bronchitis that would remit temporarily with antibiotic therapy. Sputum cultured positive for *Klebsiella pneumoniae* and treatment with Levoquin 500 mg QD #20 reduced sputum production for three weeks. Repeat sputum culture was positive for *Serratia marcensus* sensitive to Ceftin, but productive sputum and fatigue resumed following a 10 day course of Ceftin.

Bronchoscopy was performed in January of 2004 to better determine the source of recurrent bronchitis. There was no evidence of cancer recurrence (FIG. 1). Brushings of the previous tumor site revealed normal cytology. Brochoscopic washings were also sent for fungal cultures. The patient's IgG levels to *Penicillium* and *Aspergillus* were elevated, while the routine fungal cultures from bronchial washings were negative. A therapeutic trial with nizoral nasal spray 1.3% QID and sporonox 100 mg P.O. QD was partially effective. The patient reported reduced fatigue, reduced inhalant allergies and a slight reduction in volume of sputum production. In June a sputum sample was sent for fungal culture and cultures were positive for "*Penicillium* sp, MANY, *Aspergillus niger*, FEW.". Positive fungal culture after 5 months of antifungal therapy was interpreted as evidence of postradiation immunosuppression.

We considered that there was a link between *Chlamydia pneumoniae* (Cpn) and *Mycoplasma pneumoniae* (Mpn) to chronic sinusitis and asthma.

The patient was tested for and found to be positive for Mpn with IgG 2.66 (normal<0.9) and IgM 871 (normal <770), and positive for Cpn IgG 1:128 (normal<1:32). Treatment for both organisms using Amoxicillin 500 mg BID, Zithromax 250 mg Monday, Wednesday, Friday, Rifampin 300 mg BID, and metronidazole 500 mg BID 5 days on, 3 weeks off. The protocol addressed each of the three forms of Cpn: Elementary Bodies (Amoxicillin), Intracellular Replicating Bodies (Zithromax), Cryptic phase (metronidazole) and Rifampin appears to prevent the organism from changing phases.

The pulsatile dosing of metronidazole was designed to allow the Cpn to move into anaerobic cryptic phase during a three-week period which is then treated with a 5 day pulse of metronidazole. Significant bacteriolytic reactions with fever, myalgia and fatigue were reported but their intensity decreased over a four-month period of treatment. Sputum production decreased and energy levels were generally reported as high during the 3-week period without metronidazole. The patient underwent MRI evaluation of his neck on Nov. 18, 2004, 10 months after the normal bronchoscopic screening.

Figure 2:
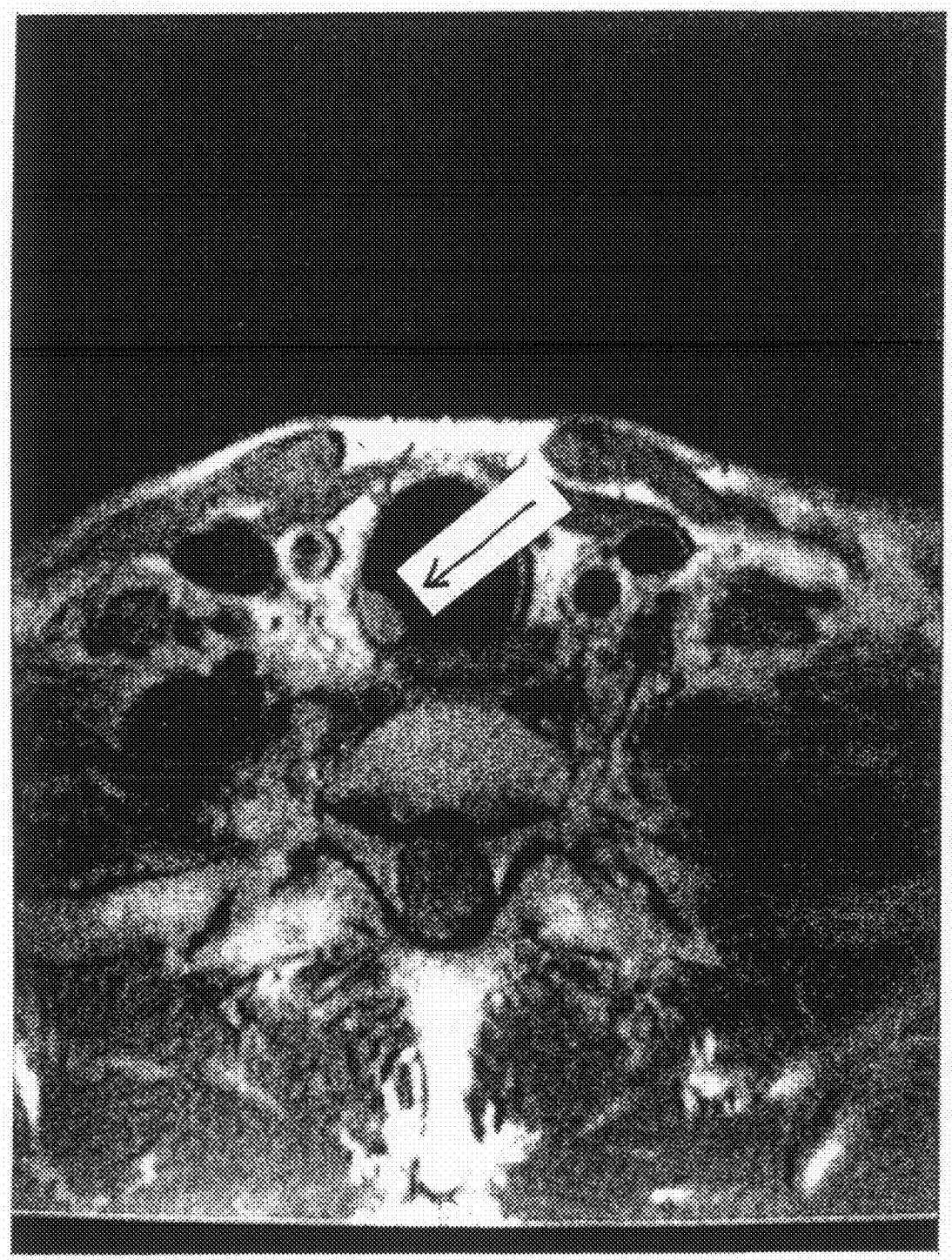
FIG. 2 depicts a coronal MRI image of the same patient as shown in FIG. 1 showing a tumor mass (arrow) in the airway wall before treatment according to this invention.

Tumor recurrence was observed 1 cm below the original tumor site (FIG. 2, coronal section, FIG. 2, sagittal section; at arrows). The MRI reported "interval development of a small 1 cm soft tissue nodule seen in the right side of the trachea at about the C7 level. This was considered suspicious for neoplasm and tumor recurrence/metastasis. There were slight ill-defined borders of the tracheal wall next to this nodule, which raised the possibility of local invasion. There was a small almost 2 cm oval structure in the low right neck suspicious for slightly enlarged lymph node. Consultation confirmed that there were no new treatments available, the maximum radiation dose had been delivered in 2000 and it was likely that laryngectomy would be necessary.

Serology revealed a mildly elevated CEA level of 3.8 (normal<2.5), consistent with ACC. A biopsy was scheduled to take place to confirm ACC in 10 days. Repeat Mpn revealed persistent and increased level of IgM 1076 (previously 871) and IgG 3.08 (previously 2.66). After 4 months of intensive antibiotic treatment, the Cpn IgG titer rose from 1:128 to 1:1256. Thus, based on these findings, we developed the following hypothesis.

LPS promotes cancer growth and stimulates the release of anti-apoptotic factors Bcl-2 and Bcl-xL. If cancer is related to LPS producing organisms, especially those with the capacity to dwell intracellularly such as Cpn, then clearing Cpn infection should restore apoptosis to the infected cancer cells and result in their death. The patient's antibiotic protocol was modified by exchanging the daily dose of Ketek for Zithromax, and the metronidazole dose was increased significantly on Nov. 21, 2004. The following day the patient reported changes in his larynx including pain, hoarseness, and warmth over the tumor site. These symptoms intensified for 6 days and gradually decreased in intensity as the biopsy date drew near.

On Dec. 3, 2004, the patient was sedated and a bronchoscopic examination was performed.

Figure 4:
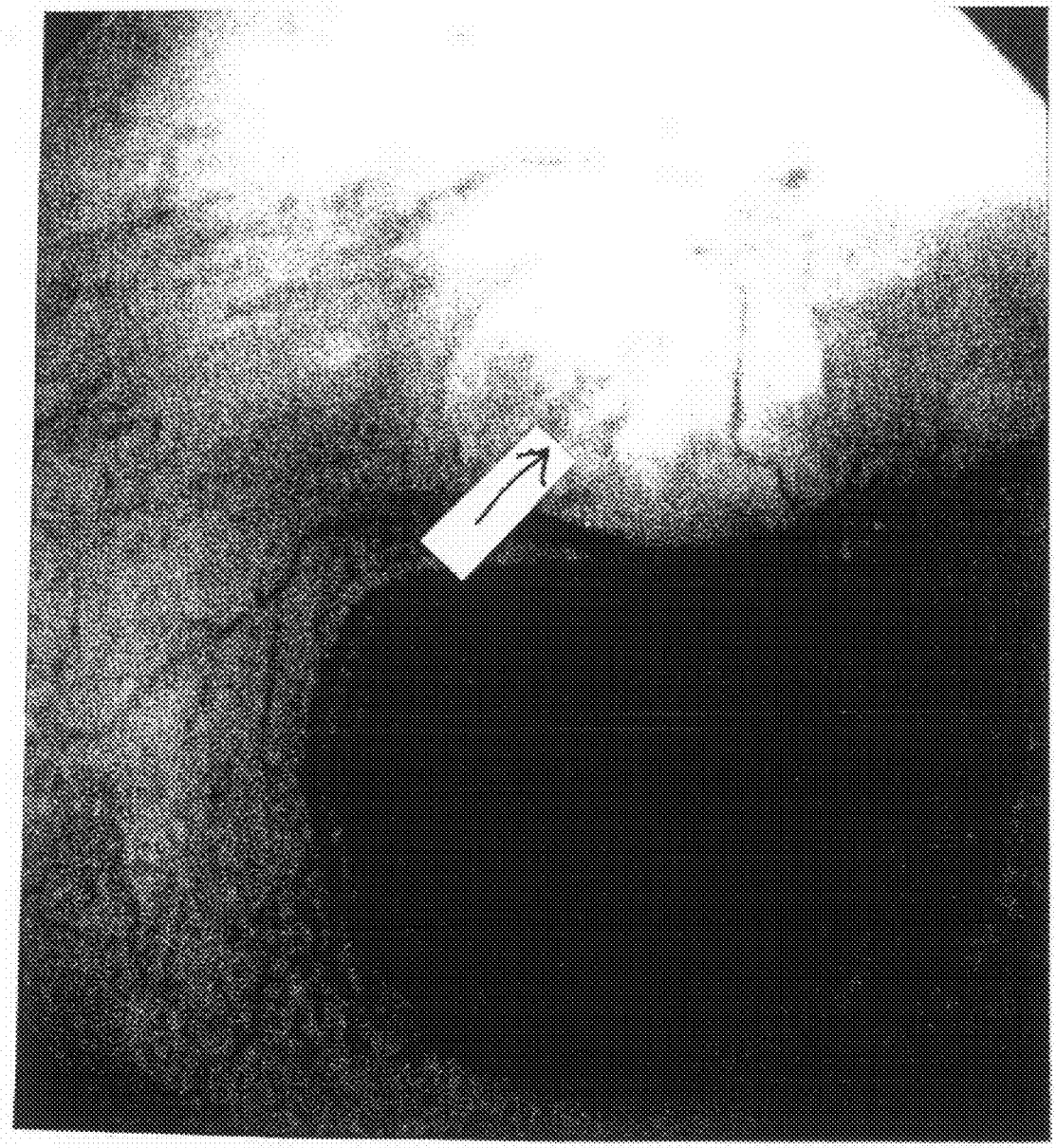
FIG. 4 depicts a photograph of the view of the same area of the patient's airway as in FIGS. 1-3, but the scar (arrow) having a smoother contour after treatment with an antibiotic according to this invention.
Figure 5:
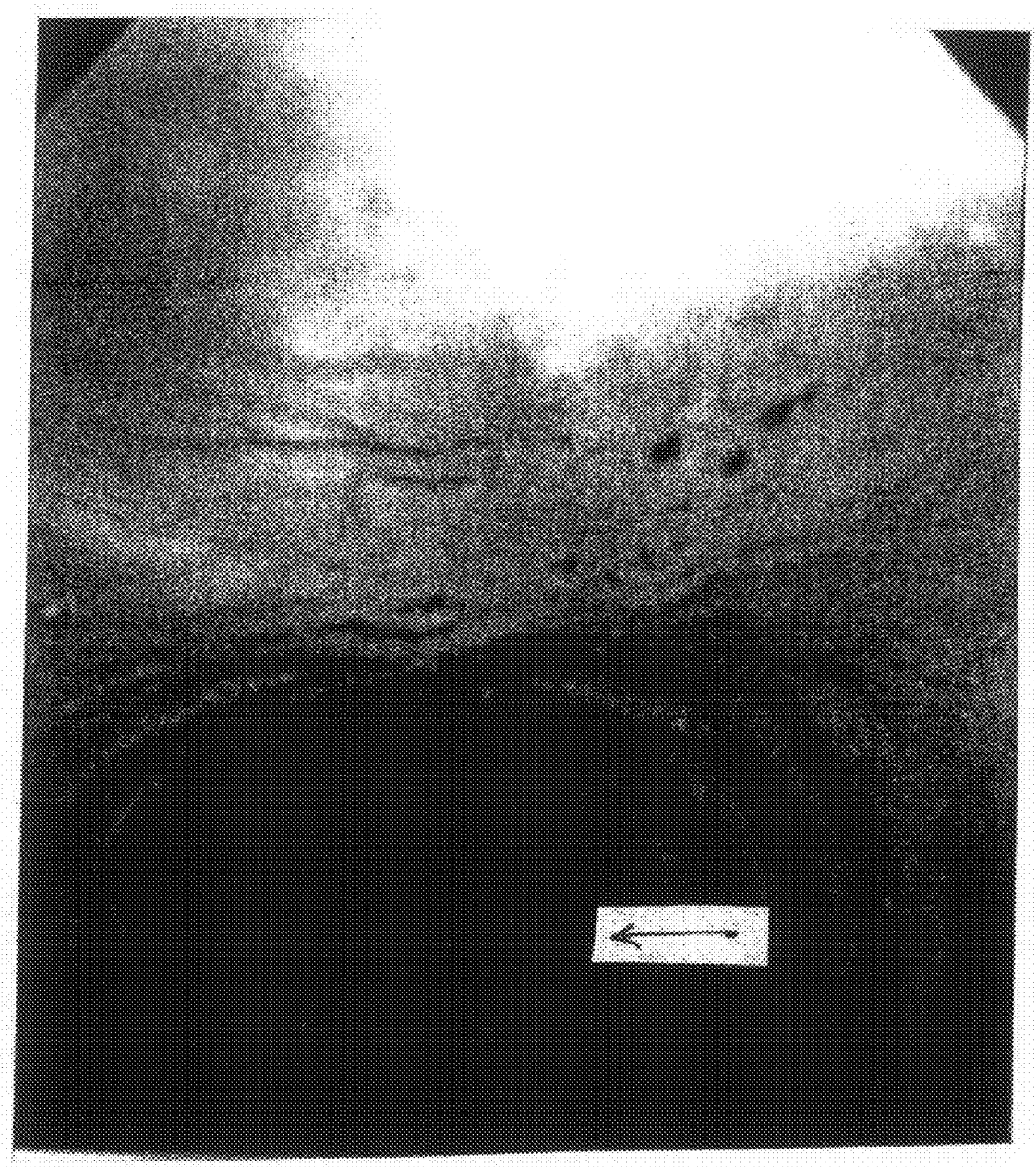
FIG. 5 depicts a photograph of the same portion of the patient's airway as in FIGS. 1-4, showing the portion of airway after treatment with antibiotic according to this invention and absence of tumor (arrow).

After the camera passed the vocal cords it was clear that the tumor was no longer present. FIG. 4 depicts a photograph of the location where the previous tumor had been, showing a smoother scar (arrow) than in the pre-treatment photo (FIG. 1, arrow). Review of the MRI from 14 days prior confirmed that the bronchoscope was in the proper location. There was no evidence of irregularity, scaring or erythema. The radiation scar from the previous bronchoscopy had a smoother appearance (see bronchoscopy Jan. 23, 2004; FIG. 1 at arrow), one that had not changed in the 3 years prior to the January bronchoscopy. The bronchoscopic image from Dec. 3, 2004 (FIG. 4) had a smooth appearance. The companion image (FIG. 5) shows a lack of any tumor on the right posterior wall 6 cm below the radiation scar (site located on upper left of image).

Figure 3:
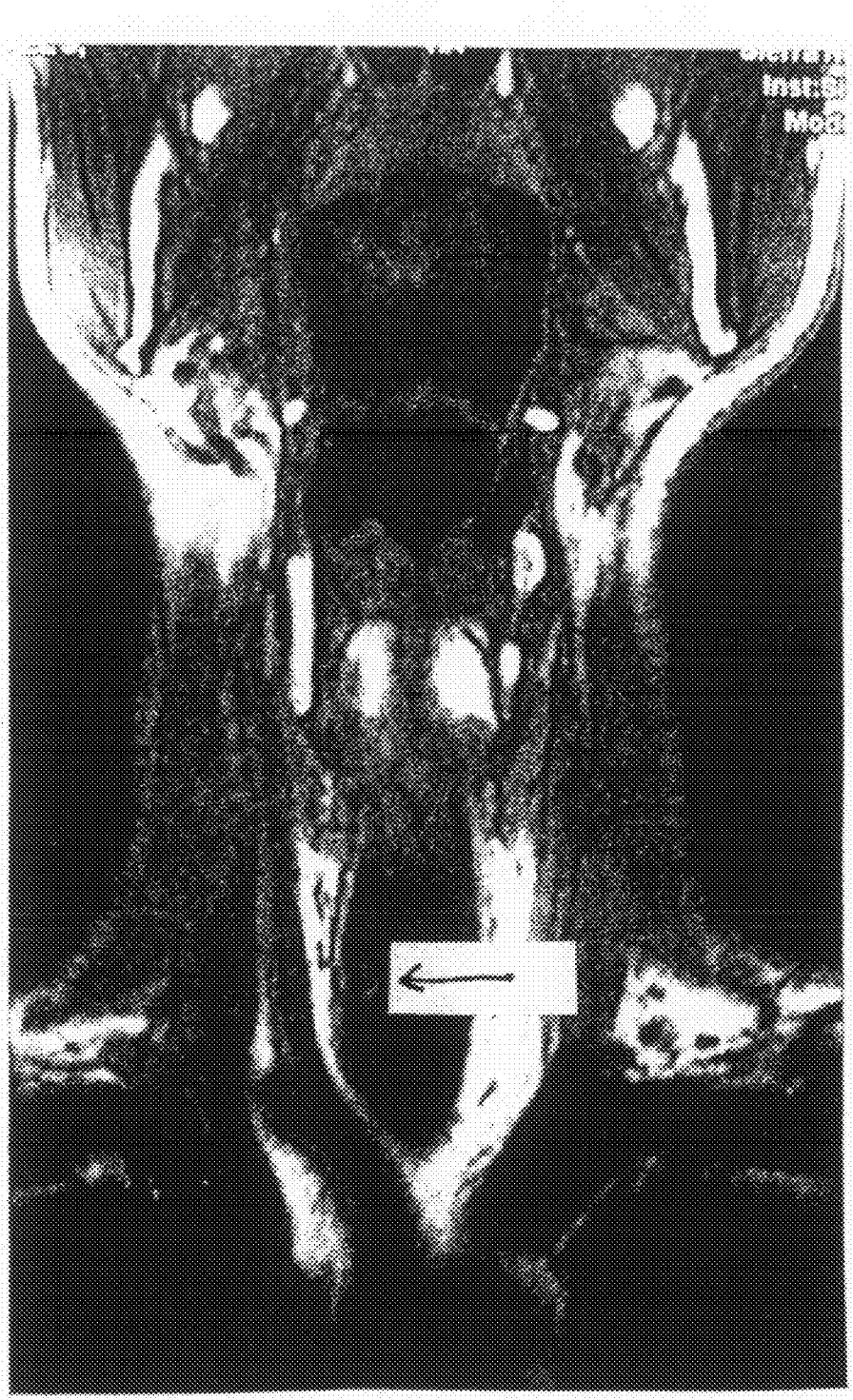
FIG. 3 depicts a sagittal MRI image of the same patient as shown in FIGS. 1-2, showing the tumor in the airway (arrow) before treatment according to this invention.
Figure 6:
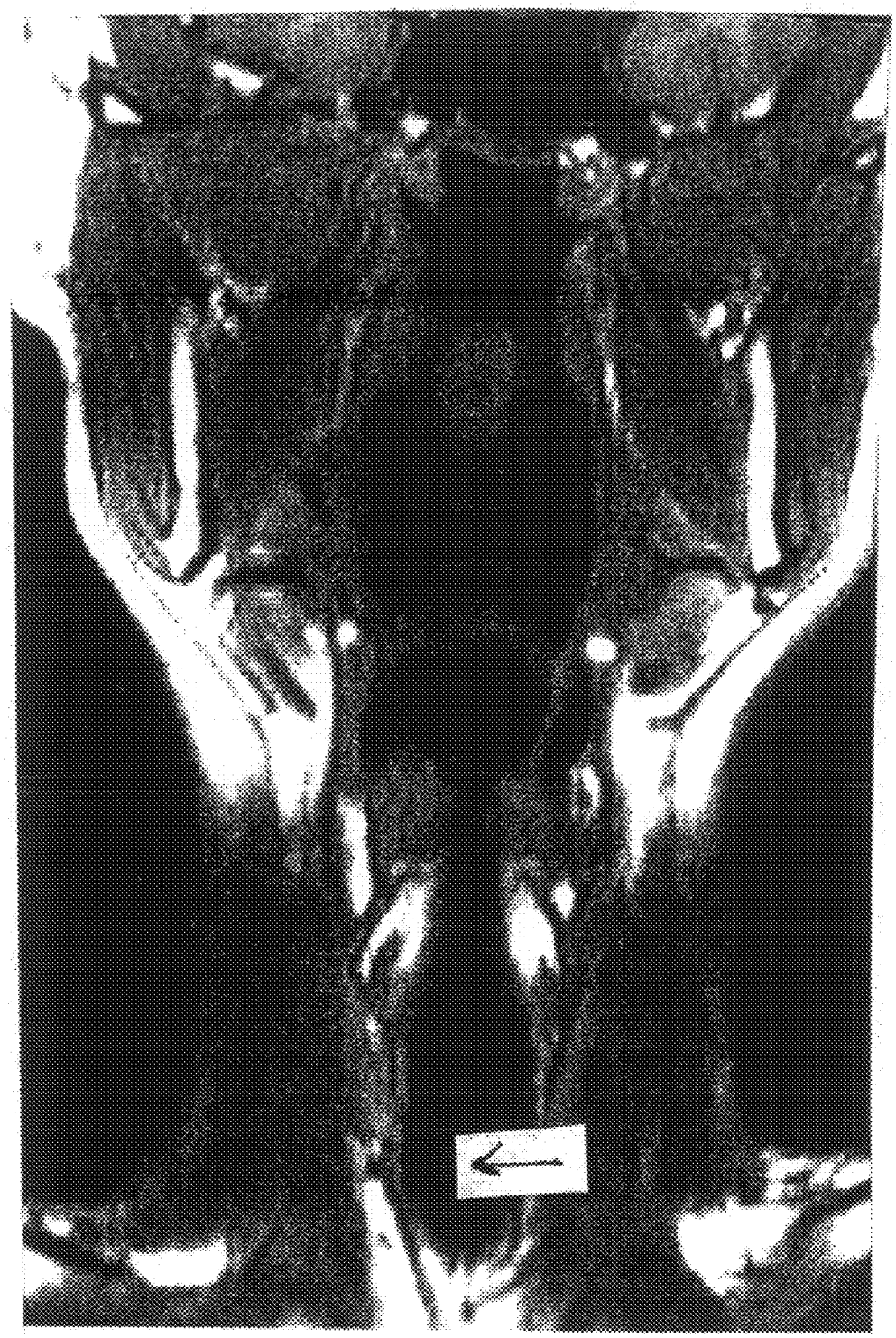
FIG. 6 depicts a sagittal MRI image of the same patient as shown in FIGS. 1-5, showing the absence of tumor in the airway (arrow) after treatment with antibiotic according to a method of this invention.

MRI images from Nov. 18, 2004 (FIGS. 2 and 3) revealed a mass with contrast enhancing vascularization. The repeat MRI from Dec. 30, 2004 (FIG. 6) showed no trace of the laryngeal mass. Seven months later, the repeat MRI from Jul. 21, 2005 showed no evidence of tumor recurrence.

Thus, with treatment using high-dose antibiotics, the soft tissue mass resembling recurrence of ACC vanished following 10 days of antibiotic treatment to eliminate Cpn, especially the cryptic anaerobic phase of the organism. Furthermore, the primary tumor site showed evidence of consolidation that did not occur during the first 3 years following radiation treatment.

The complete elimination of the suspicious mass supports the conclusion that apoptosis was initiated within this mass. The mass was not likely to be an abscess, because an abscess would not likely withstand 4 months of Amoxicillin, Zithromax, Rifampin and low intermittent doses of metronidazole. The increasing of this patient's Cpn IgG titer to 1:1256 after 4 months of treatment indicated increased Cpn antigen levels during treatment of this intracellular organism.

Interruption of apoptosis is a feature of Cpn-infected macrophages and interrupted apoptosis is common to all cancer cells. Since Cpn is ubiquitous and it is likely that the majority of people are exposed and colonized with this organism, it is likely that most people carry Cpn. If Cpn can immortalize normal cells through LPS induced HDS, it is likely that it also has an immortalizing effecting on cells that undergo genetic mutation. Most mutations lead to apoptosis, but this may not occur in Cpn-infected cells. Thus, aggressive treatment of the cryptic phase of LPS producing organisms such as Cpn can eliminate LPS and restore apoptosis to these infected tumor cells and can result in substantial, or even complete tumor regression. The aggressive neutralization of LPS and the normalization of LPS stimulated pathways and normalization of depleted cofactors are reasonable adjuncts to this approach to treatment.

Example 2

Treatment of Colon Cancer

A 55-year old male was diagnosed with metastatic stage 4-colon cancer in November of 2004. The patient reported having had walking pneumonia in 1992 and had a positive Cpn IgG of 1:64. The patient underwent tumor debulking and re-anastimoses of the colon following surgery in November immediately following diagnosis. His carcinoembryonic antigen ("CEA") level was 289 (Dec. 2, 2004), 568.4 (Dec. 21, 2004), and antibiotic therapy for Cpn was initiated on Dec. 20, 2004 with Amoxicillin. Ketek 400 mg 1 QD was initiated on Dec. 25, 2004 with Flagyl (metronidazole) 500 mg BID. He reported an immediate decrease in his abdominal pain and resolution of cervical lymphadenopathy. Abdominal distention was decreased. The patient stopped Flagyl for 24 hours and noticed a worsening of abdominal pain. CEA level was 888.6 (Jan. 7, 2005), and the antibiotic dose of Flagyl was adjusted to 500 mg 3 QD. The CEA increased to 1260 (Jan. 14, 2005) and the regimen was increased to Ketek 400 mg 2 QAM and Flagyl 500 mg 4-5 QD. The CEA decreased to 1230 (Jan. 20, 2005), demonstrating a response of the colon cancer to antibiotic treatment. The patient complained of intolerable side effects from the medication described as "feeling like I wasn't myself."

This is the first reported case of antibiotic related control of CEA levels, resolution of lymphadenopathy, and softening of abdominal distention in a patient with metastatic colon cancer. He discontinued antibiotic therapy on Jan. 19, 2005 and his final CEA was 1471.3 tested on Jan. 27, 2005. As of Feb. 10, 2005, he enrolled in hospice care, and he succumbed to metastatic colon cancer within three weeks of his discontinuation of antibiotic therapy. His intolerable symptoms of malaise and depersonalization are consistent with the neurotoxic effects of endotoxemia and the neurotoxins associated with it. It is likely that adjunctive therapy with an endotoxin-neutralizing agent such as endotoxin binding protein or calf intestine alkaline phosphatase (CLAP) would have minimized the neurotoxicity associated with the treatment of advanced LPS related HDS sequellae such as cancer. Unfortunately, these agents are not yet commercially available.

Example 3

Treatment of Pancreatic Cancer

A 48 year old female from diagnosed with stage 4-metastatic pancreatic cancer on Sep. 18, 2004 presented for evaluation Dec. 29, 2004 looking cachexic. Chemotherapy with zoloda had failed. Ascites had developed and paracentesis was performed 3 days prior to our first visit. She was having difficulty breathing and eating due to abdominal distention from ascites. Her pre-treatment rT3 was severely elevated at 0.72 (0.19-0.46). Treatment with Amoxicillin 500 mg 1 QD, Ketek 500 mg 1 QD, and Flagyl 500 mg 1-2 QD was initiated. The patient reported less abdominal pain and less ascitic fluid on Jan. 4, 2005 and was tolerating the above protocol. Her lab results from Jan. 5, 2005 showed improvement in 10 variables as compared with Dec. 27, 2004:
Sodium increased from 132 to 136,
Potassium increased from 4.4 to 4.7,
Chloride increased from 97 to 98,
Total protein increased from 5.3 to 5.7,
Albumin increased from 1.9 to 2.7,
AST decreased from 39 to 34,
ALT decreased from 26 to 17,
WBC increased from 14.8 to 20.0,
HCT increased from 24.5 to 27.2,
Platelets increased from 843 to 969 and
Neutrophils increased from 84% to 93%.

The dose of Flagyl was increased to 1500 mg on Jan. 11, 2005, but the patient's husband reported that she was becoming too ill to eat or tolerate her medications. She died on Jan. 27, 2005. Her husband stated: "She needed less vicodin after starting the antibiotics." The response to antibiotic therapy was encouraging, but full treatment using the dose that successfully induced apoptosis in adenoid cystic carcinoma in example 1 was not possible due to the severity of endotoxemic reactions with anorexia, nausea and emesis. Therefore, optimal therapy might include frequent infusion or continuous infusion of LPS neutralizing agents, along with the aforementioned blockade of LPS influenced pathways using ACE inhibitors, ARB's, 5-LOX inhibitors, COX-2 inhibitors, ascorbic acid, vitamin D, magnesium, zinc, selenium, quercetin, omega 3 oils and more.

Example 4

Treatment of Pancreatic Cancer

A 58 year old female was diagnosed with pancreatic cancer Jul. 2, 2004 had a 3 cm mass in her pancreas. A biliary stent was placed and chemotherapy was initiated Oct. 4, 2004 with Gemzar and Cisplatin, which were poorly tolerated. A repeat CT scan from Nov. 24, 2004 revealed no progression of tumor size. At an initial visit on Dec. 8, 2004, the patient was eager to discontinue all chemotherapy and she was instructed to discuss this matter with her oncologist. She was encouraged to continue chemotherapy, but she discontinued chemotherapy after feeling very ill following her Dec. 21, 2004 infusion of Gemzar. Her serology for Cpn was positive for IgG at 1:512 and IgA at 1:512 and Mycoplasma IgG was greater than 3.18. Her rT3/fT3 ratio was elevated at 8.1 (normal=4, FM=7). She started anti-Cpn therapy on Dec. 23, 2004 with Amoxicillin 500 mg BID. Three days later Ketek was added at a dose of 500 mg 1 QD and 3 days later Flagyl was added at a dose of 500 mg 1 BID.

On Jan. 3, 2005, after her 5th day of Flagyl she reported less nausea, stating "I feel like a normal person again. I'm hungry and eating again." Laboratory results from Jan. 18, 2005 revealed a lowered alkaline phosphatase level of 154 U/L, down from 207 on Jan. 4, 2005. Her platelet count normalized to 212, down from 429 on Jan. 4, 2005. Liver enzymes, still in the normal range, were slightly lower after antibiotic treatment with AST 30, and ALT 20. A CT scan performed on Feb. 1, 2005 revealed a stable tumor that has not increased in size since Nov. 24, 2004. There were no metastatic masses. The patient reported feeling better than she has felt in a long time and she is very active. Her Ketek dose was increased to 400 mg 2 QAM on Feb. 9, 2005. On Feb. 21, 2005 the patient's non-fasting blood sugar level increased to 142 mg/dl consistent with the hypoinsulinemia associated with pancreatic cancer. Transaminase levels were lower than previously tested with AST 23 and ALT 27, and Alkaline Phosphatase levels decreased from 207 on Jan. 4, 2005 to 160 U/L. The patient remained on the same dose of antibiotics until July when she was able to tolerate increasing the dose of Flagyl.

In May she reported that she was "feeling very well", her blood sugar levels were routinely near 100 mg/dl without insulin, having previously been closer to 200 mg/dl. Hgb A1C, a measure of average blood sugar levels was 5.0 ((4.6-6.2) on Jun. 21, 2005. Her lack of weight loss is impressive because cachexia is typical of pancreatic cancer and the average life expectancy for people afflicted with her tumor is only 6 months. CT scan from Jun. 10, 2005 report included: "compared to Feb. 1, 2005, there is no significant interval change". No evidence of metastasis was seen in the liver, pelvis or chest and "no lymphadenopathy" was reported. Such findings defy the natural course of pancreatic cancer. The patient has remained uncharacteristically active, her appetite is strong, and she has not lost weight over the past seven months. A CA 19-9 tumor marker from Jun. 21, 2005 was elevated above normal at 60 Hf (0-37). The previous CA 19-9 was 25 Hf on Nov. 16, 2004 following her poorly tolerated course of chemotherapy. CBC from Jun. 21, 2005 was normal (WBC 6.1, Hgb 12.8, HCT 37.5%, Plts 218K).

Chemistry panel from Jul. 12, 2005 revealed improved sodium level of 142, improved albumin of 4.2, mildly elevated AST of 40 (2-35), normal ALT of 39 (2-40) and elevated alkaline phosphatase of 239 (20-125 U/L). Glucose level was 114 mg/dl. The increased dose of metronidazole was well tolerated and the patient reported having a strong appetite on Jul. 24, 2005. Lisinopril 20 mg daily was prescribed in June to decrease NF kappa B activity, lower angiotensin as well as kinin, Bcl-2, and Bcl-xL. Vitamin C 1000 mg QID was prescribed to normalize the pro-oncogenic "inflammatory mediators" associated HDS. The patient's weight remains stable at 122-126 lbs. On July 24, the patient reported that "I feel real good" and aspirin 160 mg daily was prescribed to decrease COX-2 activity, along with omega 3 oils to decrease PGE2 levels.

A repeat CA 19-9 from Jul. 26, 2005 revealed another increase in the marker to 72 Hf, which implies either growing tumor or increased release during apoptosis. Although CA 19-9 has increased in the past month, liver enzymes have decreased to normal once again (AST 29, ALT 32). Alkaline phosphatase remains elevated, but has decreased from 239 to 229 (20-125) over the two week interval. Another CT scan is planned for next month and more aggressive treatment with a higher dose of metronidazole has been recommended with a dose that is one half the dose that was needed to successfully treat adenoid cystic carcinoma. The patient has been hesitant to increase her dose beyond her current dose. Despite the lack of resolution of this tumor, it is clear that this patient's pancreatic cancer has responded to treatment of her LPS producing infection. The availability of LPS neutralizing agents would likely allow for more aggressive and potentially more effective treatment of HDS related sequellae such as cancer. We remain optimistic that her condition will continue to respond as the dose of metronidazole is gradually increased to the dose that induced tumor apoptosis in the previously discussed case of adenoid cystic carcinoma.

More recently, her CA 19-9 level decreased 20% from the previous value a week before, indicating that the tumor was being successfully treated. She reports unusual warmth over the left upper quadrant of her abdomen and increased left upper quadrant pain that was not present prior to increasing her dose of metronidazole. These symptoms of calor and pain over the tumor site are identical to those experienced by the patient with ACC. In the case of treating ACC, these symptoms lasted for 7 days and then resolved completely along with the mass. The pancreatic cancer patient is aware that her CA 19-9 level is dropping, she is encouraged by the increased calor and pain over the tumor site and states that she feels fine and is eating 3 large meals per day. Her amylase levels are not elevated. CA 19-9 levels will be monitored closely over the next few weeks as treatment intensifies. Abdominal CT is scheduled to occur in three weeks to assess the size of her tumor.

This patient's pancreatic cancer has responded to treatment of her LPS producing infection. The availability of LPS neutralizing agents would likely allow for more aggressive and potentially more effective treatment of HDS related sequellae such as cancer. We remain optimistic that her condition will continue to respond as the dose of metronidazole is gradually increased to the dose that induced tumor apoptosis in the previously discussed case of adenoid cystic carcinoma.

Example 5

Treatment of Metastatic Breast Cancer

A 55-year old female was diagnosed with stage-4 metastatic breast cancer with bone, pelvic and lung involvement. Treatment was initiated on Jan. 23, 2005 with Amoxicillin 500 mg 1 QD, Ketek 400 mg 1 QD, Flagyl 500 mg 2 BID. The dose of Flagyl was increased to 500 mg 1 BID on Feb. 1, 2005. By Feb. 1, 2005 her wheezing and cough had decreased noticeably. Bone pain in her sacrum had increased in intensity. The improvement in pulmonary function with resolution of wheezing and resolution her dry cough was promising. In late February the dose of Flagyl was gradually increased to increase peak levels and improve tumor perfusion. After one week of increased doses of metronidazole therapy the patient developed severe depression, hypotension, hypothermia, emesis and diarrhea. All medications were discontinued, yet symptoms persisted with blood pressure of 90/60 mm Hg. Hospitalization was necessary. Work up for *Clostridium difficile* diarrhea (antibiotic associated diarrhea) was negative on three occasions. The attending physicians presumed the cause of her condition was *C. difficile* related despite the negative tests and treated her with metronidazole. Her symptoms did not remit and she was switched to Vancomycin; her symptoms gradually improved six days later. She was encouraged to discontinue antibiotic treatment and enter hospice for palliative care. Unfortunately, this patient did not resume antibiotic treatment after her bout of endotoxemia in February and she succumbed to her metastatic cancer in May 2005.

The symptoms of endotoxemia include watery diarrhea, nausea, vomiting, hypothermia and hypotension. An endotoxin assay was not available for the patient's physicians (in another State) to order during her hospitalization. A discussion was held with the patient and her husband to consider plasmapheresis to extract endotoxin during treatment. They would not be able to afford such treatment. Insurance reimbursement is excluded for experimental procedures, especially in an instance where an endotoxin assay is not available to confirm the need for plasmapheresis. At the time of this writing, the FDA has approved a new assay for endotoxin and it is available in some research centers. See the section below addressing endotoxin testing for more information. This example further illustrates the importance of managing LPS during treatment of LPS producing organisms. In the late stages of HDS related illness when it is unlikely that the patient will survive long enough to allow for the slow increase in antibiotic doses over 4-6 months recommended by some experts in the field of Cpn treatment, the use of intravenous endotoxin neutralizing agents as well as systemic blocking agents for LPS pathways is essential.

Example 6

Treatment of Systemic Lupus Erythematosus

A 40-year old female with SLE, hypocomplementemic urticarial vasculitis, and Raynaud's became symptomatic in 1996 while living in a water damaged building. Both she and her roommate developed chronic illness since they resided in this moldy structure. The patient has a sister with SLE. Features of her illness include 3+ bilateral wrist synovitis, chronic cryoglobulinemia and kidney damage with both nephrosis and occasional nephritis. Urine 24 hour protein levels were as high as 2700 milligrams per day. Stanford Nephrology consult was obtained and renal biopsy was performed in May of 2003 revealing "immune complex mediated, diffuse mesangial proliferative, and membranous glomerulonephritis, . . . 2/24 on the activity scale."

The patient elected to avoid corticosteroid therapy and it appeared that her symptoms of synovitis, hypocomplementemic urticarial rash and proteinuria were responding to treatment with hydroxychloroquine. However, iritis developed in October 2003 requiring additional immunosuppressive therapy. Trials of methotrexate and Arava were poorly tolerated and Cellcept 250 mg BID was initiated and gradually increased to 500 mg BID.

The combination of hydroxychloroquine and Cellcept was well tolerated, however the diffuse urticarial vasculitis increased in activity with ongoing elevated cryoglobulin levels, low complement levels, and elevated spot urine protein levels of >300 mg/dl despite immunosuppression. This is when treatment for LPS producing organisms and HDS was initiated. Serology for mold IgG revealed high activation of IgG against multiple strains of mold, especially *Penicillium, Cladosporium* and *Aspergillus*. Treatment with ketoconazole nasal spray, Sporonox and Nystatin along with dietary modification to minimize the intake of mold rich foods. Serum IgA for Cpn was positive (consistent with chronic recurrent infection), and IgG for Mpn was positive, and treatment with Amoxicillin, Zithromax, Rifampin, and metronidazole was initiated.

Initial reaction to the antibiotics included: fever and chills, nausea, increased salivation, crippling knee pain, knuckle swelling at MCP joints, cognitive impairment with decreased word finding. At 3 months of treatment the patient experienced temporary worsening of her rash followed by prolonged remission. After 6 months of treatment she reported that "I've never felt better." Her urticarial rash had resolved and her hematocrit has steadily improved from 33.8% (Aug. 12, 2004) to 37.0% (Nov. 4, 2004) to 38.9% (Jan. 11, 2005) to 39.3% (Feb. 17, 2005). On May 2, 2005 following 8 months of HDS treatment of LPS producing organisms her lab studies revealed the first negative cryoglobulin level in two years, positive Cpn serology with IgG 1:32 and IgA of 1:64, suppressed complement levels of C3 36.5 (87-151), and C4 2.8 (20-45). Her spot urine protein was 100 mg/dl, the lowest it has been in three years. Urine erythrocyte count was minimal at 1-5 RBC per hpf. Treatment is continuing at the time of filing this application and tapering of immunosuppressive medication will occur as immunologic parameters normalize.

Example 7

Values of rT3/fT3 in Normal Subjects and Patients with Fibromyalgia/Human Dormancy Syndrome A group of five normal, athletic, healthy females was selected based upon general fitness and levels of activity. Serum rT3 and fT3 were measured using standard methods. The average ratio of rT3 to fT3 was 4.18±1.08 (Standard Deviation). The standard error of the mean (SEM) was 0.48 (n=5).

A group of 23 patients with fibromyalgia had rT3 and fT3 levels measured using the same methods as for the group of normal individuals. The average ratio of rT3 to fT3 in this group was 6.9±4.48. The SEM was 0.93 (n=23). Therefore, patients with fibromyalgia have elevated rT3/fT3 ratios compared to normal subjects. The average increase in rT3/fT3 in patients with fibromyalgia was about 65%.

Example 8

Treatment of Human Dormancy Syndrome 211 consecutive patient charts were reviewed for response to treatment for dormancy. 51 of 211 did not follow up or participate with treatment and these patients were omitted from the study (24% attrition).

A trial of slow-release T3, oxytocin, and IM MgSO4 for approximately 3 months to reverse dormancy among fibromyalgia (n=160). Response to treatment was measured by patient symptom self-rating on a 0-10 scale evaluating energy level, pain score and overall sense of well-being.

Treatment failures=$16/160$ or 10%
Responders=$144/160$=90%
Remission was defined as a 70% response or better (ACR 70)=$66/160$=41%.

An inverse relationship was noted between patient stress level and response to treatment.

Example 9

Treatment of Dormancy in a Patient with Alzheimer's Dementia

A 73 year old retired attorney with Alzheimer's dementia was tested with the DRS-2 and found to be in the first percentile overall before T3 treatment and in the 25$^{th}$ percentile after 3 months of slow-release T3 therapy. Some parameters such as "conceptualization" increase dramatically from the 4$^{th}$ to the 50$^{th}$ percentile and "attention" improved from the 35$^{th}$ to the 89$^{th}$ percentile. The response to therapy was dramatic, and there are no other drug studies that show comparable improvement for patients with Alzheimer's dementia. Discontinuation of T3 supplementation led to a worsening of Alzheimer's symptoms. Serology for *Chlamydia pneumoniae* confirmed both IgG and IgA antibodies (consistent with chronic or relapsing infection) and treatment with antibiotic medication has provided additional improvement in cognitive function. Prophylactic treatment with low dose antifungal medication is a component of this treatment.

Example 10

Use of a Combination of Antibiotics to Treat *Chlamydia pneumoniae*-Related Rheumatoid Arthritis A 50-year old female with seropositive RA with joint swelling in her hands, elbows, knees and feet had negative serology for *Chlamydia pneumoniae* infection, along with elevated rT3/fT3 ratio and symptoms of fibromyalgia. She was initially treated with immunosuppressive medication including Prednisone 20 mg QD, Methotrexate 15 mg Qweek, antiTNF therapy with Humira injections twice monthly with limited response of less than ACR 20. Her fatigue and muscle pain improved with low dose T3 therapy. After failing immunosuppressive therapy, a course of antibiotics designed to treat *Chlamydia pneumoniae* infection was prescribed. The antibiotic protocol is consistent with that recommended by Dr. Charles Stratton of Vanderbilt University for *Chlamydia pneumoniae* infection. With the addition of a five-day course of Flagyl to daily treatment with Doxycycline and thrice weekly Zithromax, the patient experienced a dramatic worsening of her arthritis, muscle pain, and fatigue as well as fever and chills consistent with a bacteriolytic reaction. After completion of the five-day course of Flagyl, the patient experienced resolution of these symptoms and an overall improvement in all parameters of her condition. This example illustrates the unreliable nature of currently available tests for *Chlamydia pneumoniae* infection and that patients with autoimmune disease with negative tests for *Chlamydia pneumoniae* infection are likely to have seronegative *Chlamydia pneumoniae* infection and respond to antibiotics. The use of T3 and antifungal medication in conjunction with antibiotic treatment has been beneficial.

Endotoxin Testing

The FDA has recently approved an Endotoxin Activity Assay (EAA) developed by Spectral Diagnostics, Inc. for human endotoxin testing. Spectral defines the EAA's intended use in the following manner: "The EAA test is intended to be used in conjunction with other clinical information such as clinical signs, other laboratory and/or radiographic test results to aid in the risk assessment of patients on their first day of admission to the ICU for progression to severe sepsis. Patients tested on their first day of admission to the ICU where the EAA value is >0.60, are three times more likely to develop severe sepsis within the next 24 hours than subjects whose EAA values are <0.40." The control population selected for standardization of the assay is reported as the following: "We recruited 97 healthy ambulatory volunteers from the sponsor's manufacturing facility to establish normal levels for the endotoxin activity (EA) assay." The Gaussian curve for the 97 volunteers ranged from 0.1 to 0.6 "EA level", while the graph for the ICU patients they assayed from multiple test centers had values that ranged from 0.0 to 1.0 with the vast majority of patients showing levels in the 0.2 to 0.8 range. There is significant overlap with the healthy ambulatory population. For the purposes of working with ICU patients, comparison to ambulatory patient endotoxin levels may be sufficient.

However, for the purposes of using an endotoxin assay to facilitate the diagnosis of HDS and monitor therapy for LPS related infections, the control group must exclude volunteers who are infected with HDS promoting organisms. Exclusion criteria for control subjects should include a history of HDS related symptoms (i.e.—asthma, chronic sinusitis, hypertension, arthritis, fibromyalgia, cancer). Those with low probability for HDS related infections should then be tested for Cpn, Mpn, *H. pylori* using humeral assays and DNA testing as described by Charles Stratton, MD to insure that each control subject is suitable negative control. Other tests could include measurement of eosinophil cationic protein levels, NF kappa B levels, ACE and angiotensin levels to insure that Th 1 activation is not present in the negative control group. IgG testing for fungal antigens might identify those with allergic fungal syndromes that could contribute elevated endotoxin levels. Tighter control of the reference group will allow for broader application of the EAA for the purpose of identifying those at risk for HDS and it's sequellae. Defining healthy as uninflamed and uninfected or minimally infected with LPS producing organisms is a better reference point for comparison when testing those who might have HDS related conditions.

Environmental Testing

Lipopolysaccharide (LPS) is a signal used by microorganisms to impair host immunity by engaging receptors that are normally used by the host for embryonic development and hibernation. Recognition of the nature of the LPS signal should change the way we interpret our environment. For example, endotoxin is present in most food, water and air samples. Acceptable levels of endotoxin have been established for human consumption, but these guidelines were established before there was an understanding of the potential for endotoxin to contribute to HDS and related sequellae. For example, dried tobacco leaves contain large amounts of endotoxin from fungal sources. Inhaled endotoxin directly influences pulmonary cells to shift towards fetal/hibernation metabolism with what we currently refer to as "inflammatory changes," but now recognize as the anti-apoptotic molecular changes needed for the low oxygen environments of early gestation and hibernation. Chronic exposure to the LPS signal can lead to the proliferative changes observed in early gestation, findings observed in granulomatous disease and cancer. It appears that the host may become more vulnerable to LPS producing organisms after chronic environmental exposure to LPS. In the example of tobacco use, it is likely that the endotoxin on the tobacco leaves is more oncogenic than the tobacco. Environmental LPS influences the cells it stimulates and facilitates the growth of LPS producing organisms. It is likely that the facilitated growth of LPS producing organisms in smokers leads to the chronic pulmonary disease and increased cancer incidence in smokers.

Intracellular signaling from LPS producing organisms such as C.pn may have a more potent anti-apoptotic effect than extracellular LPS producing organisms. Other examples include conditions associated with organic dust inhalation. Grain dust causes a condition that Harrison's Textbook of Internal Medicine describes as "virtually identical to the characteristic findings in cigarette smokers" which is seen in grain elevator employees and workers in flour or feed mills. The grain dust contains endotoxin from mold. Farmer's Lung occurs from exposure to moldy hay, which contains LPS on airborne spores. A strain of rice was recently genetically engineered in china to produce endotoxin as a rice-synthesized pesticide. It is very effective, killing the larvae of worms as they attack the crop. Since it requires 30 minute exposure to nearly 500° F. to render endotoxin inert, it is likely that ingestion of endotoxin containing rice will significantly increase in the coming years. Ingested endotoxin that is not degraded by digestive enzymes or neutralized with bile can be absorbed and enter the blood stream. LPS is a potent signal that is ubiquitous in nature and difficult to neutralize. The volume of ingested and inhaled endotoxin has increased with the industrial revolution and it is tempting to attribute the increased incidence of diseases associated with LPS and HDS with increases in endotoxin exposure. New standards for endotoxin levels in the food and beverage industry, as well as air quality monitoring for endotoxin will be necessary to properly address HDS related sequellae.

Minimizing exposure of humans to this signal by dephosphorylating LPS in water and food prior to dispensing food and beverage products to the public is one possible solution. Modification of endotoxin with binding agents prior to ingestion might also be effective. Better testing and reporting of endotoxin levels in our food supply and careful study of animals and possibly humans who ingest various levels of endotoxin should be investigated as a possible source for the increasing incidence of HDS related diseases.

Specialty Clinics

The approach to medicine described herein is novel. As of today, there are no facilities that provide comprehensive treatment for HDS and the sequellae. This invention claims ownership of specialty clinics designed to employ the techniques described herein to reverse HDS and the sequellae. The personnel in these clinics will approach HDS related conditions with the knowledge that LPS producing organisms drive the syndrome by signaling the host to alter it's cellular functions with activation of TLR4 through LPS and other superantigens that create dormancy familiar to all humans in utero, a state that is not different from hibernation in larger animals.

Neutralization of LPS, and the use of specific cofactors to reverse trends seen in chronic conditions such as cancer and autoimmune disease are necessary to arouse cells from dormancy. The use of medication to purposefully block pathways that are activated by LPS, such as ACE inhibitors and ARB's, COX-2 inhibitors, 5-LOX inhibitors and more are helpful to arouse cells from dormancy. Elimination of LPS producing infections is also an important feature of the treatment of HDS related conditions.

Testing of endotoxin, NF kappa B, angiotensin, kinin levels or the rT3/fT3 ratio are not currently employed in the standard practice of medicine, and these tests along with assays for LPS producing organisms will be used in the specialty clinic setting for the treatment of HDS related conditions. The possible use of adeno-associated virus gene therapy to restore endogenous GLO synthesis to treat or prevent HDS related illness would also fall under the domain of the specialty clinic. Creation of CD14 or moesin blocking agents to prevent endotoxin from signaling TLR4 and other dormancy related receptors can also be seen as therapy designed for the reversal of HDS. Facilities using any part of this invention for the purposes of treating HDS or HDS related illness by reversing dormancy or neutralizing endotoxin without proper authorization and licensing will be considered to be infringing upon this invention. Health insurance companies that support the use this technology for their insured or providers without authorization and licensing from the owners of this technology are infringing upon this invention.

This invention has been described with reference to specific embodiments thereof. Other variations of the methods described herein can be made by persons of ordinary skill in the therapeutic arts without undue experimentation. All of those variations are considered to be part of this invention. All references cited herein are incorporated fully by reference.

REFERENCES

1.) Legakis I N, Golematis B C, Dourakis N, Lymberopoulou I, Mountokalakis T, Leandros E A. "Low T3 syndrome with asynchronous changes of TT3 and rT3 values in laparoscopic cholecystectomy," *Endocr Res*, May 24, 1998, (2):205-13.
2.) Chikenji T., Mizutani M., Kitsukawa Y. Anaesthesia, "Not surgical stress, induces increases in serum concentrations of reverse triiodothyronine and thyroxine during surgery," *Exp Clin Endocrinol*, 1990 April, 95(2): 217-23.
3.) Pineda G., Aguayo J., Ribalta J., Gonzalez M., and Reyes H., "Thyroid function tests in normal pregnant women (third trimester) and in pregnant women with pregnancy cholestasis or with acute hepatitis," *Rev Med Chil.*, 2000 January; 128(1):35-43.
4.) Roti E., Minelli R., and Salvi M., "Thyroid hormone metabolism in obesity," *Int J Obes Relat Metab Disorder*, June; 24, 2000, Suppl 2:S113-5.
5.) McCormack P. D., Thomas J., Malik M., Staschen C. M., "Cold stress, reverse T3 and lymphocyte function," *Alaska Med.*, July-September 1998; 40(3):55-62.
6.) Hashimoto H., Igarashi N., Miyawaki T., and Sato T., "Effects of tumor necrosis factor-alpha, interleukin-1 beta, and interleukin-6 on type I iodothyronine 5'-deiodination in rat thyroid cell line," *FRTL-5. J Interferon Cytokine Res.*, Apr. 15, 1995, (4):367-75.
7.) Shiroky J. B., Cohen M., Ballachey M. L., and Neville C., "Thyroid dysfunction in rheumatoid arthritis: a controlled prospective survey," *Ann Rheum Dis*, June 1993; 52(6): 454-6.
8.) Ijuin T., Douchi T., Yamamoto S., Ijuin Y., Nagata Y., "The relationship between maternity blues and thyroid dysfunction," *J Obstet Gynaecol Res.*, 1998 February 1998, 24(1): 49-55.
9.) Champagne F, Meaney M J. Like mother, like daughter: evidence for non-genomic transmission of parental behavior and stress responsivity. Prog Brain Res. 2001; 133:287-302.
10.) Tyson, Peter. Secrets of Hibernation. NOVA website download. 2001:p. 3.
11.) Grigg G, Beard L. Hibernation by echidnas in mild climates: hints about the evolution of endothermy? Life in the Cold. Springer Press 2000:5-19.
12.) Nichol S, Andersen N. Patterns of hibernation of echidnas in Tasmania. Life in the Cold. Springer Press 2000:21-8.
13.) Moldofsky H, et. al. Musculosketal symptoms and non-REM sleep disturbance in patients with "fibrositis syndrome" and healthy subjects. Psychosom Med. 1975 July-August; 37(4):341-51
14.) Wolfe F, Cathey M A, Kleinheksel S M. Fibrositis (Fibromyalgia) in rheumatoid arthritis. J Rheumatol. 1984 December; 11(6):814-8.
15.) Wolfe F, Smythe H A, Yunus M B, Bennett R M, Bombardier C, Goldenberg D L, Tugwell P, Campbell S M, Abeles M, Clark P, et al. The American College of Rheumatology 1990 Criteria for the Classification of Fibromyalgia. Report of the Multicenter Criteria Committee. Arthritis Rheum. 1990 February; 33(2):160-72.
16.) Smythe H A, Moldofsky H. Two contributions to understanding of the "fibrositis" syndrome. Bull Rheum Dis. 1977-78; 28(1):928-31.
17.) Mellman T A, Bustamante V, Fins A I, Pigeon W R, Nolan B. REM sleep and the early development of posttraumatic stress disorder. Am J Psychiatry. 2002 October; 159(10):1696-701.
18.) Berlant J, van Kammen D P. Open-label topiramate as primary or adjunctive therapy in chronic civilian posttraumatic stress disorder: a preliminary report. J Clin Psychiatry. 2002 January; 63(1):15-20.
19.) Gillin J C, Smith-Vaniz A, Schnierow B, Rapaport M H, Kelsoe J, Raimo E, Marler M R, Goyette L M, Stein M B, Zisook S. An open-label, 12-week clinical and sleep EEG study of nefazodone in chroniccombat-related posttraumatic stress disorder. J Clin Psychiatry. 2001 October; 62(10):789-96.
20.) Hudson J I, Mangweth B, Pope H G Jr, De Col C, Hausmann A, Gutweniger S, Laird N M, Biebl W, Tsuang M T. Family study of affective spectrum disorder. Arch Gen Psychiatry. 2003 February; 60(2):170-7.
21.) Chang L, Mayer E A, Johnson T, FitzGerald L Z, Naliboff B. Differences in somatic perception in female patients with irritable bowel syndrome with and without fibromyalgia. Pain. 2000 February; 84(2-3):297-307.
22.) Lydiard R B. Irritable bowel syndrome, anxiety, and depression: what are the links? J Clin Psychiatry. 2001; 62 Suppl 8:38-45; discussion 46-7.
23.) Kendall-Tackett K A. Physiological correlates of childhood abuse: chronic hyperarousal in PTSD, depression, and irritable bowel syndrome. Child Abuse Negl. 2000 June; 24(6):799-810.
24.) Neeck, G., Crofford, L J. Neuroendocrine pertubations in FM & CFS. Rheum Disease Clin of North Amer. 26; 4: 989-1002.
25.) Okifuji A, Turk D C. Stress and psychophysiological dysregulation in patients with fibromyalgia syndrome. Appl Psychophysiol Biofeedback. 2002 June; 27(2):129-41.
26.) Griep E N, Boersma J W, Lentjes E G, Prins A P, van der Korst J K, de Kloet E R. Function of the hypothalamic-pituitary-adrenal axis in patients with fibromyalgia and low back pain. J Rheumatol. 1998 July; 25(7):1374-81.
27.) Demitrack M A, Crofford L J. Evidence for and pathophysiologic implications of hypothalamic-pituitary-adrenal axis dysregulation in fibromyalgia and chronic fatigue syndrome. Ann N Y Acad Sci. 1998 May 1; 840:684-97.
28.) Oquendo M A, Echavarria G, Galfalvy H C, Grunebaum M F, Burke A, Barrera A, Cooper T B, Malone K M, John Mann J. Lower cortisol levels in depressed patients with comorbid post-traumatic stress disorder. Neuropsychopharmacology. 2003:28(3):591-8.
29.) Rinne T, de Kloet E R, Wouters L, Goekoop J G, de Rijk R H, van den Brink W. Fluvoxamine reduces responsiveness of HPA axis in adult female BPD patients with a history of sustained childhood abuse. Neuropsychopharmacology. 2003 January; 28(1): 126-32.
30.) Rinne T, de Kloet E R, Wouters L, Goekoop J G, DeRijk R H, van den Brink W. Hyperresponsiveness of hypothalamic-pituitary-adrenal axis to combined dexamethasone/corticotropin-releasing hormone challenge in female borderline personality disorder subjects with a history of sustained childhood abuse. Biol Psychiatry. 2002 Dec. 1; 52(11):1102-12.

31.) Marshall R D, Garakani A. Psychobiology of the acute stress response and its relationship to the psychobiology of post-traumatic stress disorder. Psychiatr Clin North Am. 2002 June; 25(2):385-95.

32.) Riedel W, Schlapp U, Leck S, Netter P, Neeck G. Blunted ACTH and cortisol responses to systemic injection of corticotropin-releasing hormone (CRH) in fibromyalgia: role of somatostatin and CRH-binding protein. Ann N Y Acad Sci. 2002 June; 966:483-90.

33.) Riedel W, Layka H, Neeck G. Secretory pattern of GH, TSH, thyroid hormones, ACTH, cortisol, FSH, and LH in patients with fibromyalgia syndrome following systemic injection of the relevant hypothalamic-releasing hormones. Z Rheumatol. 1998; 57 Suppl 2:81-7.

34.) Newport D J, et. al. Cerebrospinal Fluid Corticotropin-Releasing Factor (CRF) and Vasopressin Concentrations Predict Pituitary Response in the CRF Stimulation Test: A Multiple Regression Analysis. Neuropsychopharmacology. 2003 March; 28(3):569-576.

35.) Vermetten E, Bremner J D. Circuits and systems in stress. I. Preclinical studies. Depress Anxiety. 2002; 15(3): 126-47.

36.) Rasmusson A M, Lipschitz D S, Wang S, Hu S, Vojvoda D, Bremner J D, Southwick S M, Charney D S. Increased pituitary and adrenal reactivity in premenopausal women with posttraumatic stress disorder. Biol Psychiatry. 2001 Dec. 15; 50(12):965-77.

37.) Kizildere S, et. al. During a corticotropin-releasing hormone test in healthy subjects, administration of a beta-adrenergic antagonist induced secretion of cortisol and dehydroepiandrosterone sulfate and inhibited secretion of ACTH. Eur J Endocrinol. 2003 January; 148(1):45-53.

38.) Martinez-Lavin M, Vidal M, Barbosa R E, Pineda C, Casanova J M, Nava A. Norepinephrine-evoked pain in fibromyalgia. A randomized pilot study. BMC Musculoskelet Disord. 2002; 3(1):2.

39.) Cohen H, Neumann L, Alhosshle A, Kotler M, Abu-Shakra M, Buskila D. Abnormal sympathovagal balance in men with fibromyalgia. J Rheumatol. 2001 March; 28(3):581-9.

40.) vanOyen Witvliet C. Traumatic intrusive imagery as an emotional memory phenomenon: a review of research and explanatory information processing theories. Clin Psychol Rev. 1997; 17(5):509-36.

41.) Gurguis G N, et. al. Neutrophil beta2-adrenergic receptor coupling efficiency to Gs protein in subjects with post-traumatic stress disorder and normal controls. Psychopharmacology (Berl). 1999 April; 143(2):131-40.

42.) Orr S P, et. al. De novo conditioning in trauma-exposed individuals with and without posttraumatic stress disorder. J Abnorm Psychol. 2000 May; 109(2):290-8.

43.) Grossman D. On killing. II: The psychological cost of learning to kill. Int J Emerg Ment Health. 2001 Summer; 3(3):137-44.

44.) Larson A A, et. al. Changes in the concentrations of amino acids in the cerebrospinal fluid that correlate with pain in patients with fibromyalgia: implications for nitric oxide pathways. Pain. 2000 August; 87(2):201-11.

45.) van West D, Maes M. Neuroendocrine and immune aspects of fibromyalgia. BioDrugs. 2001; 15(8):521-31.

46.) Russell I J. The promise of substance P inhibitors in fibromyalgia. Rheum Dis Clin North Am. 2002 May; 28(2):329-42.

47.) Friedman M J. What might the psychobiology of post-traumatic stress disorder teach us about future approaches to pharmacotherapy? J Clin Psychiatry. 2000; 61 Suppl 7:44-51.

48.) Maes M, et. al. Higher serum prolyl endopeptidase activity in patients with post-traumatic stress disorder. J Affect Disord. 1999 April; 53(1):27-34.

49.) Horger B A, Roth R H. The role of mesoprefrontal dopamine neurons in stress. Crit Rev Neurobiol. 1996; 10(3-4):395-418.

50.) Staud R. Evidence of involvement of central neural mechanisms in generating fibromyalgia pain. Curr Rheumatol Rep. 2002 August; 4(4):299-305.

51.) Gracely R H, Petzke F, Wolf J M, Clauw D J. Functional magnetic resonance imaging evidence of augmented pain processing in fibromyalgia. Arthritis Rheum. 2002 May; 46(5): 1333-43.

52.) Staud R, Smitherman M L. Peripheral and central sensitization in fibromyalgia: pathogenetic role. Curr Pain Headache Rep. 2002 August; 6(4):259-66.

53.) Raymond I et. al. Incorporation of pain in dreams of hospitalized burn victims. Sleep. 2002 Nov. 1; 25(7):765-70.

54.) Mayer E A, Craske M, Naliboff B D. Depression, anxiety, and the gastrointestinal system. J Clin Psychiatry. 2001; 62 Suppl 8:28-36; discussion 37.

55.) Weisberg R B, et. al. Nonpsychiatric illness among primary care patients with trauma histories and posttraumatic stress disorder. Psychiatr Serv. 2002 July; 53(7):848-54.

56.) Allgulander C, Kasper S. Coping with somatic comorbidities: striving for complete recovery. Psychopharmacol Bull. 2002 Summer; 36 Suppl 2:103-11.

57.) Goettl V M, et. al Reduced basal release of serotonin from the ventrobasal thalamus of the rat in a model of neuropathic pain. Pain. 2002 September; 99(1-2):359-66.

58.) Legangneux E, Mora J J, Spreux-Varoquaux O, Thorin I, Herrou M, Alvado G, Gomeni C. Cerebrospinal fluid biogenic amine metabolites, plasma-rich platelet serotonin and [3H]imipramine reuptake in the primary fibromyalgia syndrome. Rheumatology (Oxford). 2001 March; 40(3):290-6.

59.) Butterfield M I, Becker M, Marx C E. Post-traumatic Stress Disorder in Women: Current Concepts and Treatments. Curr Psychiatry Rep. 2002 December; 4(6):474-86.

60.) Strawn J R, Ekhator N N, Anthenelli R M, Baker D G, Maxwell R A, Hill K K, Geracioti T D. Intra- and inter-individual relationships between central and peripheralserotonergic activity in humans: a serial cerebrospinal fluid sampling study. Life Sci. 2002 Jul. 26; 71(10):1219-25.

61.) Seedat S, Stein D J, Ziervogel C, Middleton T, Kaminer D, Emsley R A, Rossouw W. Comparison of response to a selective serotonin reuptake inhibitor in children, adolescents, and adults with posttraumatic stress disorder. J Child Adolesc Psychopharmacol. 2002 Spring; 12(1):37-46.

62.) Bennett R M. Adult growth hormone deficiency in patients with fibromyalgia. Curr Rheumatol Rep. 2002 August; 4(4):306-12.

63.) Moldofsky H. Management of sleep disorders in fibromyalgia. Rheum Dis Clin North Am. 2002 May; 28(2):353-65.

64.) Paiva E S, Deodhar A, Jones K D, Bennett R. Impaired growth hormone secretion in fibromyalgia patients: evidence for augmented hypothalamic somatostatin tone. Arthritis Rheum. 2002 May; 46(5):1344-50.

65.) Bremner J D, Krystal J H, Southwick S M, Charney D S. Noradrenergic mechanisms in stress and anxiety: II. Clinical studies. Synapse. 1996 May; 23(1):39-51.

66.) Anderberg U M, Uvnas-Moberg K. Plasma oxytocin levels in female fibromyalgia syndrome patients. Z Rheumatol. 2000 December; 59(6):373-9.

67.) Samborski W, Stratz T, Schochat T, Mennet P, Muller W. [Biochemical changes in fibromyalgia] Z Rheumatol. 1996 May-June; 55(3):168-73. German.

68.) Teicher M H, Andersen S L, Polcari A, Anderson C M, Navalta C P. Developmental neurobiology of childhood stress and trauma. Psychiatr Clin North Am. 2002 June; 25(2):397-426, vii-viii.

69.) Maes M, Lin A H, Bonaccorso S, Goossens F, Van Gastel A, Pioli R, Delmeire L, Scharpe S. Higher serum prolyl endopeptidase activity in patients with post-traumatic stress disorder. J Affect Disord. 1999 April; 53(1):27-34.

70.) Henry J P, Wang S. Effects of early stress on adult affiliative behavior. Psychoneuroendocrinology. 1998 November; 23(8):863-75.

71.) Wang S. Traumatic stress and attachment. Acta Physiol Scand Suppl. 1997; 640:164-9.

72.) Pall M L. Common etiology of posttraumatic stress disorder, fibromyalgia, chronic fatigue syndrome and multiple chemical sensitivity via elevated nitricoxide/peroxynitrite. Med Hypotheses. 2001 August; 57(2): 139-45.

73.) Pall M L, Satterle J D. Elevated nitric oxide/peroxynitrite mechanism for the common etiology of multiple chemical sensitivity, chronic fatigue syndrome, and posttraumatic stress disorder. Ann N Y Acad Sci. 2001 March; 933:323-9.

74.) Wik G, Fischer H, Bragee B, Kristianson M, Fredrikson M. Retrosplenial cortical activation in the fibromyalgia syndrome. Neuroreport. 2003 Mar. 24; 14(4):619-21.

75.) Gracely R H, Petzke F, Wolf J M, Clauw D J. Functional magnetic resonance imaging evidence of augmented pain processing in fibromyalgia. Arthritis Rheum. 2002 May; 46(5): 1333-43.

76.) Kwiatek R, Barnden L, Tedman R, Jarrett R, Chew J, Rowe C, Pile K. Regional cerebral blood flow in fibromyalgia: single-photon-emission computed tomography evidence of reduction in the pontine tegmentum and thalami. Arthritis Rheum. 2000 December; 43(12):2823-33.

77.) Pissiota A, Frans O, Fernandez M, von Knorring L, Fischer H, Fredrikson M. Neurofunctional correlates of posttraumatic stress disorder: a PET symptom provocation study. Eur Arch Psychiatry Clin Neurosci. 2002 April; 252(2):68-75.

78.) Osuch E A, Benson B, Geraci M, Podell D, Herscovitch P, McCann U D, Post R M. Regional cerebral blood flow correlated with flashback intensity in patients with post-traumatic stress disorder. Biol Psychiatry. 2001 Aug. 15; 50(4):246-53.

79.) Pitman R K, Shin L M, Rauch S L. Investigating the pathogenesis of posttraumatic stress disorder with neuroimaging. J Clin Psychiatry. 2001; 62 Suppl 17:47-54.

80.) Mirzaei S, Knoll P, Keck A, Preitler B, Gutierrez E, Umek H, Kohn H, Pecherstorfer M. Regional cerebral blood flow in patients suffering from post-traumatic stress disorder. Neuropsychobiology. 2001; 43(4):260-4.

81.) Park D C, Glass J M, Minear M, Crofford L J. Cognitive function in fibromyalgia patients. Arthritis Rheum. 2001 September; 44(9):2125-33.

82.) Glass J M, Park D C. Cognitive dysfunction in fibromyalgia. Curr Rheumatol Rep. 2001 April; 3(2):123-7.

83.) Leavitt, F. Cognitive and dissociative manifestations in fibromyalgia. J Clin. Rheum 2002; 8(2):77-84.

84.) Stein M B, Kennedy C M, Twamley E W. Neuropsychological function in female victims of intimate partner violence with and without posttraumatic stress disorder. Biol Psychiatry. 2002 Dec. 1; 52(11):1079-88.

85.) Ferguson E, Cassaday H J. Theoretical accounts of Gulf War Syndrome: from environmental toxins to psychoneuroimmunology and neurodegeneration. Behav Neurol. 2001-2002; 13(3-4):133-47.

86.) Orr S P, Metzger L J, Pitman R K. Psychophysiology of post-traumatic stress disorder. Psychiatr Clin North Am. 2002 June; 25(2):271-93.

87.) Horner M D, Hamner M B. Neurocognitive functioning in posttraumatic stress disorder. Neuropsychol Rev. 2002 March; 12(1):15-30.

88.) Cohen H, Neumann L, Alhosshle A, Kotler M, Abu-Shakra M, Buskila D. Abnormal sympathovagal balance in men with fibromyalgia. J Rheumatol. 2001 March; 28(3): 581-9.

89.) Bell I R, Baldwin C M, Russek L G, Schwartz G E, Hardin E E. Early life stress, negative paternal relationships, and chemical intolerance in middle-aged women: support for a neural sensitization model. J Womens Health. 1998 November; 7(9): 1135-47.

90.) Martinez-Lavin M, Hermosillo A G, Mendoza C, Ortiz R, Cajigas J C, Pineda C, Nava A, Vallejo M. Orthostatic sympathetic derangement in subjects with fibromyalgia. J Rheumatol. 1997 April; 24(4):714-8.

91.) Moldofsky H. Sleep and pain. Sleep Med Rev. 2001 October; 5(5):385-396.

92.) Fitzcharles M A, Costa D D, Poyhia R. A study of standard care in fibromyalgia syndrome: a favorable outcome. J Rheumatol. 2003 January; 30(1):154-9.

93.) Nicassio P M, Moxham E G, Schuman C E, Gevirtz R N. The contribution of pain, reported sleep quality, and depressive symptoms to fatigue in fibromyalgia. Pain. 2002 December; 100(3):271-9.

94.) Ferguson E, Cassaday H J. Theoretical accounts of Gulf War Syndrome: from environmental toxins to psychoneuroimmunology and neurodegeneration. Behav Neurol. 2001-2002; 13(3-4):133-47.

95.) Taylor R R, Jason L A. Chronic fatigue, abuse-related traumatization, and psychiatric disorders in a community-based sample. Soc Sci Med. 2002 July; 55(2):247-56.

96.) Sansone R A, Gaither G A, Sansone L A. Childhood trauma and adult somatic preoccupation by body area among women in an internal medicine setting: a pilot study. Int J Psychiatry Med. 2001; 31(2):147-54.

97.) Maquet D, Croisier J L, Renard C, Crielaard J M. Muscle performance in patients with fibromyalgia. Joint Bone Spine. 2002 May; 69(3):293-9.

98.) Park J H, Niermann K J, Olsen N. Evidence for metabolic abnormalities in the muscles of patients with fibromyalgia. Curr Rheumatol Rep. 2000 April; 2(2):131-40.

99.) Borman P, Celiker R, Hascelik Z. Muscle performance in fibromyalgia syndrome. Rheumatol Int. 1999; 19(1-2):27-30.

100.) Weisberg R B, Bruce S E, Machan J T, Kessler R C, Culpepper L, Keller M B. Nonpsychiatric illness among primary care patients with trauma histories and posttraumatic stress disorder. Psychiatr Serv. 2002 July; 53(7):848-54.

101.) Hamner M B, Hitri A. Plasma beta-endorphin levels in post-traumatic stress disorder: a preliminary report on response to exercise-induced stress. J Neuropsychiatry Clin Neurosci. 1992 Winter; 4(1):59-63.

102.) Khvatova E M, Samartzev V N, Zagoskin P P, Prudchenko I A, Mikhaleva I I. Delta sleep inducing peptide (DSIP): effect on respiration activity in ratbrain mitochondria and stress protective potency under experimental hypoxia. Peptides. 2003 February; 24(2):307-311.

103.) Pongratz D E, Sievers M. Fibromyalgia-symptom or diagnosis: a definition of the position. Scand J Rheumatol Suppl. 2000; 113:3-7.

104.) Pongratz D E, Spath M. Morphologic aspects of fibromyalgia. Z Rheumatol. 1998; 57 Suppl 2:47-51.

105.) McDermid A J, Rollman G B, McCain G A. Generalized hypervigilance in fibromyalgia: evidence of perceptual amplification. Pain. 1996 August; 66(2-3): 133-44.

106.) Clauw D J. Potential mechanisms in chemical intolerance and related conditions. Ann N Y Acad Sci. 2001 March; 933:235-53.

107.) Sherman J J, Turk D C, Okifuji A. Prevalence and impact of posttraumatic stress disorder-like symptoms on patients with fibromyalgia syndrome. Clin J Pain. 2000 June; 16(2): 127-34.

108.) Mertin P, Mohr P B. Incidence and correlates of post-trauma symptoms in children from backgrounds of domestic violence. Violence Vict. 2002 October; 17(5):555-67.

109.) Norris F H, Weisshaar D L, Conrad M L, Diaz E M, Murphy A D, Lbanez G E. A qualitative analysis of post-traumatic stress among Mexican victims of disaster. J Trauma Stress. 2001 October; 14(4):741-56.

110.) Dalgleish T, Moradi A R, Taghavi M R, Neshat-Doost H T, Yule W. An experimental investigation of hypervigilance for threat in children and adolescents with post-traumatic stress disorder. Psychol Med. 2001 April; 31(3):541-7.

111.) Alfici S, Sigal M, Landau M. Primary fibromyalgia syndrome—a variant of depressive disorder? Psychother Psychosom. 1989; 51(3): 156-61.

112.): Muris P, Merckelbach H, Peeters E. The links between the Adolescent Dissociative Experiences Scale (A-DES), fantasy proneness, and anxiety symptoms. J Nerv Ment Dis. 2003 January; 191(1):18-24.

113.) Malta L S, Blanchard E B, Taylor A E, Hickling E J, Freidenberg B M. Personality disorders and posttraumatic stress disorder in motor vehicle accident survivors. J Nerv Ment Dis. 2002 November; 190(11):767-74.

114.) Brosschot J F, Aarsse H R. Restricted emotional processing and somatic attribution in fibromyalgia. Int J Psychiatry Med. 2001; 31(2):127-46.

115.) Bryant R A, Harvey A G. Gender differences in the relationship between acute stress disorder and posttraumatic stress disorder following motor vehicle accidents. Aust N Z J Psychiatry. 2003 April; 37(2):226-229.

116.) Gershuny B S, Cloitre M, Otto M W. Peritraumatic dissociation and PTSD severity: do event-related fears about death and control mediate their relation? Behav Res Ther. 2003 February; 41(2):157-66.

117.) Van Houdenhove B, Neerinckx E, Onghena P, Vingerhoets A, Lysens R, Vertommen H. Daily hassles reported by chronic fatigue syndrome and fibromyalgia patients in tertiary care: a controlled quantitative and qualitative study. Psychother Psychosom. 2002 July-August; 71(4): 207-13

118.) Cohen H, Neumann L, Haiman Y, Matar M A, Press J, Buskila D. Prevalence of post-traumatic stress disorder in fibromyalgia patients: Overlapping syndromes or post-traumatic fibromyalgia syndrome? Semin Arthritis Rheum. 2002 August; 32(1):38-50.

119.) Tsigos C, Chrousos G P. Hypothalamic-pituitary-adrenal axis, neuroendocrine factors and stress. J Psychosom Res. 2002 October; 53(4):865-71.

120.) Lee H A, Gabriel R, Bale A J, Bolton P, Blatchley N F. Clinical findings of the second 1000 UK Gulf War veterans who attended the Ministry of Defence's Medical Assessment Programme. J R Army Med Corps. 2001 June; 147 (2):153-60.

121.) Ehlert U, Gaab J, Heinrichs M. Psychoneuroendocrinological contributions to the etiology of depression, post-traumatic stress disorder, and stress-related bodily disorders: the role of the hypothalamus-pituitary-adrenal axis. Biol Psychol. 2001 July-August; 57(1-3):141-52.

122.) Van Houdenhoven, B et. al. Victimization in chronic fatigue syndrome & fibromyalgia: a controlled study on prevalence and characteristics. Psychosomatics 2001; January-February; 42(1): 21-28 Usually family of origin and correlation not seen in RA and MS patients.

123.) Taylor, M. et. al. The prevalence of sexual abuse in women with FM. Arthritis & Rheum. 1995; 38:2. 229-234.

124.) Goldberg, R. et al. Relationship between traumatic events in childhood and chronic pain. Disability & Rehab. 1999; 21:1. 23-30. Harvard study "Child traumatic events are significantly related to chronic pain. Child abuse is broader than physical and sexual abuse."

125.) Finestone H M, Stenn P, Davies F, Stalker C, Fry R, Koumanis J. Chronic pain and health care utilization in women with a history of childhood sexual abuse. Child Abuse Negl. 2000 April; 24(4):547-56.

126.) Mathilde, H et. al. Sexual and physical abuse in women with FM. Arthritis & Rheum. 1995; 38:2.235-241.

127.) Kreidler M C, Briscoe L A, Beech R R. Pharmacology for post-traumatic stress disorder related to childhood sexual abuse: a literature review. Perspect Psychiatr Care. 2002 October-December; 38(4):135-45.

128.) Bifulco A, Moran P M, Baines R, Bunn A, Stanford K. Exploring psychological abuse in childhood: II. Association with other abuse and adult clinical depression. Bull Menninger Clin. 2002 Summer; 66(3):241-58.

129.) Lekander M, Fredrikson M, Wik G. Neuroimmune relations in patients with fibromyalgia: a positron emission tomography study. Neurosci Lett. 2000 Mar. 24; 282(3): 193-6.

130.) Hernanz W, Valenzuela A, Quijada J, Garcia A, de la Iglesia J L, Gutierrez A, Povedano J, Moreno I, Sanchez B. Lymphocyte subpopulations in patients with primary fibromyalgia. J Rheumatol. 1994 November; 21(11):2122-4.

131.) Jara L J, Lavalle C, Fraga A, Gomez-Sanchez C, Silveira L H, Martinez-Osuna P, Germain B F, Espinoza L R. Prolactin, immunoregulation, and autoimmune diseases. Semin Arthritis Rheum. 1991 April; 20(5):273-84.

132.) Inoue-Sakurai C, Maruyama S, Morimoto K. Posttraumatic stress and lifestyles are associated with natural killer cell activity in victims of the Hanshin-Awaji earthquake in Japan. Prev Med. 2000 November; 31(5):467-73.

133.) Lyman C P, Willis J S, Malan A, Wang L C H. Hibernation and Torpor in Mammals and Birds. Academic Press 1982: pp 1-31.

134.) Kayser Ch. The Physiology of Natural Hibernation. Pergamon Press 1961. pp 1-44.

135.) Harlow H J, Lohuis T, Beck T, Iaizze P. Muscle strength in overwintering bears. Nature Feb. 22, 2001(409):997.

136.) Sterling, J. Polar Bears. Ann Arbor: University of Michigan Press, 1988.

137.) Hissa R, Siekkinen J, Hohtola E, Saarela S, Hakala A, Pudas J. Seasonal patterns in the physiology of the European brown bear (*Ursus arctos arctos*) in Finland. Comp Biochem Physiol A Physiol. 1994 November; 109(3):781-91.

138.) Muller A E. Aspects of social life in the fat-tailed dwarf lemur (*Cheirogaleus medius*): inferences from body weights and trapping data. Am J Primatol. 1999 November; 49(3):265-80.

139.) Kohrle J, Schomburg L, Drescher S, Fekete E, Bauer K. Rapid stimulation of type I 5'-deiodinase in rat pituitaries by 3,3',5-triiodo-L-thyronine. Mol Cell Endocrinol. 1995 Feb. 27; 108(1-2):17-21.

140.) Altshuler L L, Bauer M, Frye M A, Gitlin M J, Mintz J, Szuba M P, Leight K L, Whybrow P C. Does thyroid supplementation accelerate tricyclic antidepressant response? A review and meta-analysis of the literature. Am J Psychiatry. 2001 October; 158(10):1617-22.

141.) Brzezinska-Slebodzinska E, Slebodzinski A B, Styczynska E. Stimulatory effect of melatonin on the 5'-monodeiodinase activity in the liver, kidney, and brown adipose tissue during the early neonatal period of the rabbit. J Pineal Res. 1998 April; 24(3):137-41.

142.) Nedvidkova J, Papezova H, Haluzik M, Schreiber V. Interaction between serum leptin levels and hypothalamo-hypophyseal-thyroid axis in patients with anorexia nervosa. Endocr Res. 2000 May; 26(2):219-30.

143.) Bianco A C, Nunes M T, Hell N S, Maciel R M. The role of glucocorticoids in the stress-induced reduction of extrathyroidal 3,5,3'-triiodothyronine generation in rats. Endocrinology. 1987 March; 120(3): 1033-8.

144.) Baumgartner A, Hiedra L, Pinna G, Eravci M, Prengel H, Meinhold H. Rat brain type II 5'-iodothyronine deiodinase activity is extremely sensitive to stress. J Neurochem. 1998 August; 71(2):817-26.

145.) Eravci M, Pinna G, Meinhold H, Baumgartner A. Effects of pharmacological and nonpharmacological treatments on thyroid hormone metabolism and concentrations in rat brain. Endocrinology. 2000 March; 141(3):1027-40.

146.) 1: Everson C A, Nowak T S Jr. Hypothalamic thyrotropin-releasing hormone mRNA responses to hypothyroxinemia induced by sleep deprivation. Am J Physiol Endocrinol Metab. 2002 July; 283(1):E85-93.

147.) Burr W A, Ramsden D B, Griffiths R S, Black E G, Hoffenberg R, Meinhold H, Wenzel K W. Effect of a single dose of dexamethasone on serum concentrations of thyroid hormones. Lancet. 1976 Jul. 10; 2(7976):58-61.

148.) Schlienger J L, Kauffmann J P, Bur F, Sapin R, Demangeat C, Hollender L F. [Effect of surgery on the level of total and free thyroid hormones, reverse T3 and TSH] Ann Endocrinol (Paris). 1982 July-September; 43(4):259-68. French.

149.) Johansson G, Laakso M L, Karonen S L, Peder M. Examination stress affects plasma levels of TSH and thyroid hormones differently in females and males. Psychosom Med. 1987 July-August; 49(4):390-6.

150.) Vitek V, Shatney C H. Thyroid hormone alterations in patients with shock and injury. Injury. 1987 September; 18(5):336-41.

151.) Langer P, Balazova E, Vician M, Martino E, Jezova D, Michalikova S, Moravec R. Acute development of low T3 syndrome and changes in pituitary-adrenocortical function after elective cholecystectomy in women: some differences between young and elderly patients. Scand J Clin Lab Invest. 1992 May; 52(3):215-20.

152.) Torpy D J, Tsigos C, Lotsikas A J, Defensor R, Chrousos G P, Papanicolaou D A. Acute and delayed effects of a single-dose injection of interleukin-6 on thyroid function in healthy humans. Metabolism. 1998 October; 47(10): 1289-93.

153.) Cerillo A G, Sabatino L, Bevilacqua S, Farneti P A, Scarlattini M, Forini F, Glauber M. Nonthyroidal illness syndrome in off-pump coronary artery bypass grafting. Ann Thorac Surg. 2003 January; 75(1):82-7.

154.) Joosten K F, de Kleijn E D, Westerterp M, de Hoog M, Eijck F C, Hop W C J, Voort E V, Hazelzet J A, Hokken-Koelega A C. Endocrine and metabolic responses in children with meningoccocal sepsis: striking differences between survivors and nonsurvivors. J Clin Endocrinol Metab. 2000 October; 85(10):3746-53.

155.) Shigematsu H, Shatney C H. [The effect of triiodothyronine (T3) and reverse triiodothyronine (rT3) on canine hemorrhagic shock] Nippon Geka Gakkai Zasshi. 1988 October; 89(10):1587-93. Japanese.

156.) Kales J D, Kales A. Nocturnal psychophysiological correlates of somatic conditions and sleep disorders. Int J Psychiatry Med. 1975; 6(1-2):43-62.

157.) Carpenter A C, Timiras P S. Sleep organization in hypo- and hyperthyroid rats. Neuroendocrinology. 1982 June; 34(6):438-43.

158.) Goto S, Billmire D F, Grosfeld J L. Hypothyroidism impairs colonic motility and function. An experimental study in the rat. Eur J Pediatr Surg. 1992 February; 2(1): 16-21.

159.) Lake-Bakaar G. Hypothyroidism and functional bowel disease. Am J Med. 1990 March; 88(3):312-3.

160.) Meserve L A, Leathem J H. Development of hypothalamic-pituitary-adrenal response to stress in rats made hypothyroid by exposure to thiouracil from conception. J Endocrinol. 1981 September; 90(3):403-9.

161.) Ban Y, Ban Y, Taniyama M, Hara H, Abe T, Katagiri T. Aberrant luteinizing hormone-releasing hormone-stimulated adrenocorticotropic hormone secretion in a patient with pituitary hyperplasia due to primary hypothyroidism. Endocr J. 2000 August; 47(4):481-6.

162.) Tohei A, Watanabe G, Taya K. Hypersecretion of corticotrophin-releasing hormone and arginine vasopressin in hypothyroid male rats as estimated with push-pull perfusion. J Endocrinol. 1998 February; 156(2):395-400.

163.) Tohei A, Akai M, Tomabechi T, Mamada M, Taya K. Adrenal and gonadal function in hypothyroid adult male rats. J Endocrinol. 1997 January; 152(1):147-54.

164.) Fommei E, Iervasi G. The role of thyroid hormone in blood pressure homeostasis: evidence from short-term hypothyroidism in humans. J Clin Endocrinol Metab. 2002 May; 87(5): 1996-2000.

165.) Foley C M, McAllister R M, Hasser E M. Thyroid status influences baroreflex function and autonomic contributions to arterial pressure and heart rate. Am J Physiol Heart Circ Physiol. 2001 May; 280(5):H2061-8.

166.) Savard P, Blanchard L M, Merand Y, Bedard P, Dussault J H, Dupont A. Influences of both thyroid and bovine growth hormones on substance P, thyrotropin-releasing hormone, serotonin and 5-hydroxyindoleacetic acid contents in the lumbar spinal cord of developing rats. Brain Res. 1984 March; 315(1):105-10.

167.) Aronin N, Coslovsky R, Chase K. Hypothyroidism increases substance P concentrations in the heterotopic anterior pituitary. Endocrinology. 1988 June; 122(6):2911-4.

168.) Jones P M, Ghatei M A, Steel J, O'Halloran D, Gon G, Legon S, Burrin J M, Leonhardt U, Polak J M, Bloom S R. Evidence for neuropeptide Y synthesis in the rat anterior pituitary and the influence of thyroid hormone status: comparison with vasoactive intestinal peptide, substance P, and neurotensin. Endocrinology. 1989 July; 125(1):334-41.

169.) Bauer M, Heinz A, Whybrow P C. Thyroid hormones, serotonin and mood: of synergy and significance in the adult brain. Mol Psychiatry. 2002; 7(2): 140-56.

170.) Badaue-Passos D Jr, Ventura R, Silva L F, Olivares E L, Reis L C. Effect of brain serotoninergic stimulation on sodium appetite of euthyroid and hypothyroid rats. Exp Physiol. 2003 March; 88(Pt 2):251-60.

171.) Moreno B, Rodriguez-Manzaneque J C, Perez-Castillo A, Santos A. Thyroid hormone controls the expression of insulin-like growth factor I receptor gene at different levels in lung and heart of developing and adult rats. Endocrinology. 1997 March; 138(3):1194-203.

172.) Brown M R, Parks J S, Adess M E, Rich B H, Rosenthal I M, Voss T C, VanderHeyden T C, Hurley D L. Central hypothyroidism reveals compound heterozygous mutations in the Pit-1 gene. Horm Res. 1998; 49(2):98-102.

173.) Adan R A, Cox J J, van Kats J P, Burbach J P. Thyroid hormone regulates the oxytocin gene. J Biol Chem. 1992 Feb. 25; 267(6):3771-7.

174.) Dellovade T L, Zhu Y S, Pfaff D W. Thyroid hormones and estrogen affect oxytocin gene expression in hypothalamic neurons. J Neuroendocrinol. 1999 January; 11(1):1-10.

175.) Colin I M, Kopp P, Zbaren J, Haberli A, Grizzle W E, Jameson J L. Expression of nitric oxide synthase III in human thyroid follicular cells: evidence for increased expression in hyperthyroidism. Eur J Endocrinol. 1997 June; 136(6):649-55.

176.) Quesada A, Sainz J, Wangensteen R, Rodriguez-Gomez I, Vargas F, Osuna A. Nitric oxide synthase activity in hyperthyroid and hypothyroid rats. Eur J Endocrinol. 2002 July; 147(1):117-22.

177.) Constant E L, de Voider A G, Ivanoiu A, Bol A, Labar D, Seghers A, Cosnard G, Melin J, Daumerie C. Cerebral blood flow and glucose metabolism in hypothyroidism: a positron emission tomography study. J Clin Endocrinol Metab. 2001 August; 86(8):3864-70.

178.) Kinuya S, Michigishi T, Tonami N, Aburano T, Tsuji S, Hashimoto T. Reversible cerebral hypoperfusion observed with Tc-99m HMPAO SPECT in reversible dementia caused by hypothyroidism. Clin Nucl Med. 1999 September; 24(9):666-8.

179.) Baldini I M, Vita A, Mauri M C, Amodei V, Carrisi M, Bravin S, Cantalamessa L Psychopathological and cognitive features in subclinical hypothyroidism. Prog Neuropsychopharmacol Biol Psychiatry. 1997 August; 21(6):925-35.

180.) Ganguli M, Burmeister L A, Seaberg E C, Belle S, DeKosky S T. Association between dementia and elevated TSH: a community-based study. Biol Psychiatry. 1996 Oct. 15; 40(8):714-25.

181.) Lambert M, Thissen J P, Doyen C, Col J, Coche E. Orthostatic hypotension associated with hypothyroidism. Acta Clin Belg. 1984; 39(1):48-50.

182.) Morrow L B. How thyroid disease presents in the elderly. Geriatrics. 1978 April; 33(4):42-5.

183.) Hylander B, Ekelund L G, Rosenqvist U. The cardiovascular response at rest and during exercise in hypothyroid subjects to thyroxine substitution. Clin Cardiol. 1983 March; 6(3):116-24.

184.) Enriquez J A, Fernandez-Silva P, Garrido-Perez N, Lopez-Perez M J, Perez-Martos A, Montoya J. Direct regulation of mitochondrial RNA synthesis by thyroid hormone. Mol Cell Biol. 1999 January; 19(1):657-70.

185.) Martinez B, del Hoyo P, Martin M A, Arenas J, Perez-Castillo A, Santos A. Thyroid hormone regulates oxidative phosphorylation in the cerebral cortex and striatum of neonatal rats. J Neurochem. 2001 September; 78(5):1054-63.

186.) Sasaki N, Takahashi A, Nakano N, Saito T. [A case of 'hallucination of soliloquy' with hypothyroidism induced Hashimoto disease. Meaning of psychopathological research about symptomatic psychosis] Seishin Shinkeigaku Zasshi. 2001; 103(2):185-96. Japanese.

187.) Dorn L D, Burgess E S, Dichek H L, Putnam F W, Chrousos G P, Gold P W. Thyroid hormone concentrations in depressed and nondepressed adolescents: group differences and behavioral relations. J Am Acad Child Adolesc Psychiatry. 1996 March; 35(3):299-306.

188.) Simon N M, Blacker D, Korbly N B, Sharma S G, Worthington J J, Otto M W, Pollack M H. Hypothyroidism and hyperthyroidism in anxiety disorders revisited: new data and literature review. J Affect Disord. 2002 May; 69(1-3):209-17.

189.) Provinciali M, Muzzioli M, Di Stefano G, Fabris N. Recovery of spleen cell natural killer activity by thyroid hormone treatment in old mice. Nat Immun Cell Growth Regul. 1991; 10(4):226-36.

190.) Marsh J A, Merlino P G, Staeheli P. The effects of triodothyronine and thymulin on avian NK cytolytic activity. Int Immunopharmacol. 2001 September; 1(9-10):1823-30.

191.) Haraldsen L, Soderstrom-Lauritzsen V, Nilsson G E. Oxytocin stimulates cerebral blood flow in rainbow trout (*Oncorhynchus mykiss*) through a nitric oxide dependent mechanism. Brain Res. 2002 Mar. 1; 929(1):10-4.

192.) Young L J, Lim M M, Gingrich B, Insel T R. Cellular mechanisms of social attachment. Horm Behav. 2001 September; 40(2):133-8.

193.) Altemus M, deuster P, Galliven E, Carter C S, Gold P. Suppression of hypothalamic-pituitary-adrenal axis responses to stress in lactating women. J of Clin Endocrin. 1995:80(10):2954-59.

194.) Buck M, Squire T, Andrews M. Coordinate expression of the PDK4 gene: a means of regulating fuel selection in a hibernating mammal. Physiol Genomics 8; 5-13, 2002.

195.) Kilduff T S, Krilowics B, Milsom W K, Trachsel L, Wang L C H. Sleep and mammalian Hibernation: Homolous adaptations and homolous processes?. Sleep, 16(4):372-386.

196.) Deboer T, Tobler I. The djungarian hamster is sleep deprived during daily torpor. Life in the Cold. Springer Press 2000: pp 251-260.

197.) Saitongdee P, Milner P, Loesch A, Knight G, Burnstock G. Electron-immunocytochemical studies of perivascular nerves of mesenteric and renal arteries of golden hamsters during and after arousal from hibernation. J Anat. 1999 July; 195 (Pt 1):121-30.

198.) Taguchi T, Ikeda K, Shono T, Goto S, Kubota M, Kawana T, Hirose R, Toyohara T. Autonomic innervation of the intestine from a baby with megacystis microcolon intestinal hypoperistalsis syndrome: I. Immunohistochemical study. J Pediatr Surg. 1989 December; 24(12):1264-6.

199.) Shinomura Y, Himeno S, Kurokawa M, Takahashi S, Kuroshima T, Okuno M, Kanayama S, Tsuji K, Higashimoto Y, Tarui S. Release of vasoactive intestinal peptide by intraduodenal infusion of HCl or fat and intramuscular injection of neostigmine in man. Hepatogastroenterology. 1985 June; 32(3):129-32.

I claim:

1. A method for treating cancer in a patient, comprising the steps of:
   (a) identifying a patient susceptible to therapy, said patient having:
      (i) a diagnosed cancer;
      (ii) a rT3/fT3 ratio of greater than about 4; and
      (iii) at least one other finding selected from the group consisting of
      elevated levels of: fungal or bacterial DNA, *Chlamydia*, *Mycoplasma*, alpha 2-macroglobulin, alpha-fetoprotein, angiotensin II, Bcl-2, Bcl-XL c-fos, c-jun, ACE activity, CGRP, calsequestrin, CEA, catalase cathespin B, cIAP-2, connexin 43, CRF, COX-2 activity, d-dimer, endothelin-1, endotoxin, enkephalin, epithelial growth factor, FADD, fas ligand and/or fas/APO 1 ratio, FLIP, gastrin, ghrelin, glutathione peroxidase, FABP, heme oxygenase-1, hormone-sensitive lipase, HSP70, HIF-1, ICAM-1, IGF-1, IL-6, INK, kallikrein, kinin, lipoxygenase, MAPK, Mcl-1, activation of the moesin-ezrin system, neuropeptide Y, neurotensin, NF kappa B, pancreatic triglyceride lipase, PDK, peptide YY, prolactin, prostcyclin, PGE2, protein kinase C, resistin, rT3, serine protease, substance P, superoxide dismutatse, survivin, TNF alpha, tyrosine hydroxylase, UCP2 & 3 activity, VIP, vasopressin or VEGF;

decreased levels of alpha-1 antitrypsin, antithrombin III, apolipoprotein, ascorbic acid, Bax, Bid, Bad, CI-esterase inhibitor, caspase, caveolin-1, cystatin, cytochrome-c oxidase, dopamine, Factor V, fT3, glyceraldehyde-3-phosphate dehydrogenase activity, GSH/GSSG ratio, IGFBP, junB, melatonin, Na/K ATPase activity, nitric oxide, orexin-A, hypocretin-1, altered oxytocin levels, decreased p53, PARP, PPAR gamma, ROCK-2, secretin, serotonin or TRAIL activity;

(b) initiating therapy with at least one antibiotic until at least one sign of endotoxemia is observed;

(c) continuing step (b) until at least one sign of endotoxemia decreases; and (d) adding at least one additional antibiotic to the regimen of step (b).

2. The method of claim 1, further comprising inhibiting the enzyme 5-D1 to elevate serum fT3 levels, so that the ratio of serum rT3/fT3 decreases to below about 4.

3. The method of claim 1, further comprising stimulating the enzyme 5'-D1 to increase ff3 production so that the ratio of serum rT3/fT3 decreases to below about 4.

4. The method of claim 1, further comprising inhibiting the enzyme 5-D1 and stimulating at least one of the enzymes 5'-D2 and 5'-D1 so that the ratio of serum rT3/fT3 is below about 4.

5. The method of claim 1, further comprising administering T3 to decrease the ratio of serum rT3/fT3 to below about 4.

6. The method of claim 1, wherein said patient has elevated levels of fungus or *Chlamydia pneumoniae*, fungus or *Chlamydia pneumoniae* DNA or immunofluorescent stains for fungus or *Chlamydia pneumoniae* in the thyroid gland.

7. The method of claim 1, wherein said first antibiotic is amoxicillin, zithromax, rifampin, doxycycline and metronidazole.

8. The method of claim 1, wherein said additional antibiotic is flagyl.

9. The method of claim 1, further comprising:

(a) administering amoxicillin or doxycycline 100 mg/2×/day or minocyn 100 mg 2×/day for 2 weeks; then (b) along with the antibiotic of step (a), administering zithromax 250-500 mg 3×/week or ketek 100 mg 2×/day for 2 weeks; then (c) administering metronidazole 500 mg 2×/day for 0.5 days; then (d) ceasing treatment with metronidazole for two weeks while maintaining steps (a) & (b) above; then (e) administering metronidazole 500 mg 2×/day for 5 days on, 2 weeks off until symptoms of endotoxemia decrease; then (f) administering metronidazole at a dose of 1000 mg 2×/day or 2000 mg 2×/day until tumor cell death occurs.

10. The method of claim 1, further comprising administering one or more agents to reduce adverse effects of endotoxin selected from the group consisting of an endotoxin binding or endotoxin neutralizing agent, an agent to inhibit NF kappa B activity, an agent to inhibit ACE, Vitamin C, Vitamin B 12, an agent to inhibit cyclooxygenase-2 (COX-2), an omega-3 oil, an agent to inhibit interleukin-6 (IL-6), an agent to inhibit metalloproteinase activity or an agent to protect the liver from endotoxin damage.

11. The method of claim 10, wherein said agent to inhibit metalloproteinase activity is doxycycline or minocycline.

12. The method of claim 10, wherein said endotoxin neutralizing agent is selected from the group consisting of charcoal; cholestyramine, pancrelipase and pancreatic digestive enzymes containing amylase, protease, and lipase at a concentration of 20,000 units per dose.

13. The method of claim 10, wherein said agent to inhibit NF kappa B is selected from the group consisting of lisinopril, an angiotensin converting enzyme (ACE) inhibitor, quercetin, Vitamin D, magnesium, zinc, and selenium.

14. The method of claim 10, wherein said agent to reduce prostaglandin E2 is omega 3 oil, Vitamin C or a non-steriodal antiinflammatory (NSAID).

15. The method of claim 14, wherein said NSAID is a cyclooxygenase inhibitor or aspirin.

16. The method of claim 10, wherein said agent to inhibit interleukin-6 (IL-6) is hydroxychloroquine.

17. The method of claim 10, wherein said agent to protect the liver is silymarin.

18. The method of claim 1, further comprising at least one of chemotherapy and radiation therapy.

* * * * *

UNITED STATES PATENT AND TRADEMARK OFFICE
CERTIFICATE OF CORRECTION

PATENT NO. : 8,343,488 B2
APPLICATION NO. : 12/322488
DATED : January 1, 2013
INVENTOR(S) : Michael Powell It is certified that error appears in the above-identified patent and that said Letters Patent is hereby corrected as shown below:

Col. 47, line 8, delete "INK" and insert --JNK--

Col. 47, line 35, delete "ff3" and insert --fT3--

Col. 48, line 9, delete "0.5" and insert --5--

Signed and Sealed this
Twenty-eighth Day of May, 2013

Teresa Stanek Rea
*Acting Director of the United States Patent and Trademark Office*